United States Patent [19]
Heki et al.

[11] Patent Number: 5,906,008
[45] Date of Patent: May 25, 1999

[54] DISPOSABLE DIAPER

[75] Inventors: Yukio Heki, Hyogo; Takashi Hiuke, Hirakata, both of Japan

[73] Assignee: The Procter & Gamble Company, Cincinnati, Ohio

[21] Appl. No.: 08/913,486

[22] PCT Filed: Apr. 3, 1996

[86] PCT No.: PCT/US96/02922

§ 371 Date: Sep. 19, 1997

§ 102(e) Date: Sep. 19, 1997

[87] PCT Pub. No.: WO96/29038

PCT Pub. Date: Sep. 26, 1996

[30] Foreign Application Priority Data

Mar. 22, 1995 [JP] Japan ...................................... 7-62795

[51] Int. Cl.⁶ .................................................. A61F 13/56
[52] U.S. Cl. ................................ 2/400; 2/110; 604/385.1; 604/389
[58] Field of Search ................................... 2/1, 2, 46, 53, 2/54, 55, 56, 57, 69, 69.5, 75, 80, 78.1, 110, 78.2, 111, 78.3, 78.4, 83, 109, 400, 401, 402, 403, 404, 405, 406, 407, 408; 604/385.1, 387, 388, 389, 390, 391, 393, 394, 398, 396

[56] References Cited

U.S. PATENT DOCUMENTS

| H1674 | 8/1997 | Ames et al. | 604/389 |
|---|---|---|---|
| 5,358,500 | 10/1994 | Lavon et al. | 604/385.2 |
| 5,397,318 | 3/1995 | Dreier | 604/385.2 |
| 5,496,298 | 3/1996 | Kuepper et al. | 604/389 |
| 5,653,704 | 8/1997 | Buell et al. | 604/385.2 |

*Primary Examiner*—Jeanette Chapman
*Attorney, Agent, or Firm*—Kevin D. Hogg; E. Kelly Linman; Jacobus C. Rasser

[57] ABSTRACT

This invention is a disposable diaper (1) having an absorbent (3), a pair of ears (6) projecting in opposite directions from the opposite side edges of one longitudinal end portion of the absorbent part (3), respectively, and one fastening means (7) attached to the oblique side edges of the ears (6), respectively. The oblique side edges of the ears (6) are inclined to extend at a predetermined angle to the longitudinal center axis of the absorbent (3), the fastening means (7) are attached to the oblique side edges, respectively, each oblique side edge having first oblique side edge section and second oblique side edge section, each ear (6) has a stress relaxing structure, in which a tensile stress smaller than that induced in the peripheral portion of the ear (6) is induced, in a portion thereof other than the peripheral portion, and each fastening means is attached to the ear (6) in a pulling section of the oblique side edge in order to distribute tensile forces.

25 Claims, 20 Drawing Sheets

DISPOSABLE DIAPER

FIELD OF THE INVENTION

The present invention relates to a disposable diaper having an absorbent part, a pair of ear parts projecting in opposite directions from the side edges of one longitudinal end portion of the absorbent part, and one fastening means provided on the oblique side edges of the ear parts, respectively, and capable of effectively distributing tensile forces applied to the absorbent part by the fastening means around the waist and around the legs to prevent the leakage of liquid excrements through spaces between the edges of the disposable diaper and the wearer's waist and legs and of giving comfort to the wearer.

BACKGROUND OF THE INVENTION

A generally known disposable diaper comprises an absorbent part for covering the wearer's crotch, formed by sandwiching an absorbent core between a top sheet and a back sheet, a pair of ear parts projecting in opposite directions from the side edges of one longitudinal end portion of the absorbent part so as to lap around the wearer's waist, and two fastening means provided on the side edges of the ear parts, respectively. When using this disposable diaper, the disposable diaper is put on the wearer in an ordinary manner, and then the fastening means are attached to portions of the absorbent part lapping around the waist, on the opposite sides of the fastening means, respectively, to hold the disposable diaper on the wearer. When thus put on the wearer, the disposable diaper must fit to the wearer's waist and legs so that any spaces through which liquid excrements will leak may not be formed between the disposable diaper and the wearer's waist and legs. When putting the disposable diaper provided with the fastening means provided on the side edges of the ear parts, respectively, on the wearer, it is difficult to concentrate the tensile forces applied to the absorbent part by the fastening means effectively on portions of the absorbent part lapped around the wearer's waist and legs; that is, spaces are formed around the wearer's legs if the disposable diaper is fitted to the wearer's waist, or spaces are formed around the wearer's waist and the disposable diaper cannot lap fitly around the wearer's waist if the disposable diaper is fitted to the wearer's legs.

Various improvements have been proposed to solve such problems and to improve the fit of a disposable diaper to the wearer's waist and legs. Techniques for improving the fit of a disposable diaper to both the waist and the legs are disclosed in U.S. Pat. No. 4,680,030 to Aled, et al., U.S. Pat. No. 4,826,499 to Ahr and U.S. Pat. No. 4,937,887 to Schreiner, which use two pairs of fastening means attached to a pair of ear parts projecting in opposite directions from a portion of the disposable diaper to be lapped around the waist, respectively. These prior art disposable diapers, however, require troublesome work for handling the tow pairs of fastening means and there is room for improvement in those prior art disposable diapers.

Techniques eliminated such a disadvantage are disclosed in U.S. Pat. No. 4,911,702 to O'Leary and U.S. Pat. No. 4,857,067 to Wood, which use two fastening means attached to two ear parts, respectively, and capable of effectively concentrating the tensile forces applied thereto on portions of the absorbent part lapped around the waist and the legs. However, these techniques mention nothing about the positions of the two fastening means to distribute the tensile forces applied to the two fastening means effectively and directly around the waist and the legs and about the positions of the two fastening means to distribute the tensile forces applied to the two fastening means around the waist and the legs at an intentionally determined distribution ratio.

A disposable diaper disclosed in, for example, Japanese Utility Model Laid-open (Kokai) No. 59-73305 has a main part, ear parts projecting in opposite directions from the side edges of the main part, respectively, and two fastening means attached to the side edges of the ear parts parallel to the longitudinal axis of the main part respectively, so as to extend obliquely to the transverse edge of the longitudinal end of a portion of the main part on the back side to distribute the tensile forces applied to the main part by the two fastening means effectively around the waist and the legs. Although the two fastening means are attached to the ear parts, respectively, so as to extend obliquely to the transverse edge of the longitudinal end of a portion of the main part on the back side, the fastening means are pulled involuntarily in a direction perpendicular to the side edges of the ear parts because the fastening means are attached to the side edges of the ear parts parallel to the longitudinal axis of the main part, respectively, and, consequently, the tensile forces applied to the main part by the two fastening means cannot be properly distributed around the waist and the legs at an intended distribution ratio.

SUMMARY OF THE INVENTION

Accordingly, it is a first object of the present invention to provide a disposable diaper having an absorbent part provided with fastening means disposed so as to be pulled necessarily obliquely to the axis of the disposable diaper and capable of effectively and directly concentrating tensile forces applied thereto on portions of the absorbent part lapped around the waist and the legs, respectively.

A second object of the present invention is to provide a disposable diaper having an absorbent part provided with fastening means disposed so that tensile forces applied thereto are distributed around the waist and the legs at a desired distribution ratio, respectively.

A third object of the present invention is to provide a disposable diaper having an absorbent part having leg lapping sections to be lapped around the legs, provided with elastic fitting members, respectively, and fastening means disposed so that the tensile forces applied thereto are concentrated effectively and directly on a portion of the absorbent part to be lapped around the waist and on the elastic fitting members.

A fourth object of the present invention is to provide a disposable diaper having an absorbent part having a waist lapping section and leg lapping sections to be lapped around the waist and the legs provided with elastic fitting members, respectively, and fastening means disposed so that the tensile forces applied thereto are concentrated effectively and directly on the elastic fitting members.

In a first aspect of the present invention, a disposable diaper comprises: an absorbent part formed by sandwiching an absorbent core between a top sheet and a back sheet so that the absorbent core may corresponds to the wearer's crotch when the disposable diaper is put on the wearer; a pair of ear parts projecting in opposite directions from the opposite side edges of one longitudinal end portion of the absorbent part, respectively; and one fastening means attached to the side edges of the ear parts, respectively. In this disposable diaper, the oblique side edges of the ear parts to which the fastening means are attached, respectively, are inclined so as to extend at a predetermined angle to the longitudinal center axis of the disposable diaper, the fastening means are attached to the ear parts so as to extend perpendicularly to the corresponding oblique side edges, respectively, each ear part has a stress relaxing structure, in which a tensile stress smaller than that which is induced in the peripheral portion of the ear part is induced, in a portion thereof other than the peripheral portion, and each fastening means is attached to the ear part in a pulling section of the oblique side edge of the ear part, overlapping at least part of a first side edge section extending on the side of one longitudinal end edge of the absorbent part corresponding to the ear part from a first boundary line extending from the one longitudinal end edge so as to be tangent to the stress relaxing structure, and a second side edge section extending on the side of the lateral center axis of the absorbent part perpendicular to the longitudinal center axis of the absorbent part from a second boundary line extending from a point on the side edge of the absorbent part at which the lower end of the ear part joins to the absorbent part so as to be tangent to the stress relaxing structure.

In a second aspect of the present invention, a disposable diaper comprises; an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge, respectively, a crotch lapping section extending between the first and the second waist lapping section; a pair of ear parts projecting from the opposite side edges of the first waist lapping section of the absorbent part; and one fastening means attached to the oblique side edges of the ear parts, respectively. In this disposable diaper, the oblique side edges of the ear parts to which the fastening means are attached, respectively, are inclined at a predetermined angle to the longitudinal center axis of the disposable diaper, the fastening means are attached to the ear parts so as to extend perpendicularly to the corresponding oblique side edges, respectively, each ear part has a stress relaxing structure, in which a tensile stress smaller than that which is induced in the peripheral portion of the ear part is induced, in a portion thereof other than the peripheral portion, a portion of the first waist lapping section, extending on the side of the first longitudinal end edge from a first boundary line extending from a point on the first longitudinal end edge so as to be tangent to the stress relaxing structure is a waist lapping component force distributing region to which a component of a tensile force applied to the fastening means acts directly, a section of the oblique side edge of the ear part corresponding to the waist lapping component force distributing region is a first oblique side edge section, a portion of the first waist portion, extending on the side of the crotch portion from a second boundary line extending from a point on the side edge of the absorbent part at which the lower end of the ear part joins to the absorbent part so as to be tangent to the stress relaxing structure is a leg lapping component force distributing region to which a component of a tensile force applied to the fastening means acts directly, a section of the oblique side edge of the ear part corresponding to the leg lapping component force distributing region is a second oblique side edge section, and each fastening means is attached to the ear part in a pulling section of the oblique side edge of the ear part, overlapping at least part of the first side edge section and the second side edge section.

In a third aspect of the present invention, a disposable diaper comprises; an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge, respectively, a crotch lapping section extending between the first and the second waist lapping section; elastic leg fastening means extended along the opposite longitudinal side edges of the crotch lapping part; a pair of ear parts projecting from the opposite side edges of the first waist lapping section of the absorbent part; and one fastening means attached to the oblique side edges of the ear parts, respectively. In this disposable diaper, the oblique side edges of the ear parts to which the fastening means are attached, respectively, are inclined at a predetermined angle to the longitudinal center axis of the disposable diaper, the fastening means are attached to the ear parts so as to extend perpendicularly to the corresponding oblique side edges, respectively, each ear part has a stress relaxing structure, in which a tensile stress smaller than that which is induced in the peripheral portion of the ear part is induced, in a portion thereof other than the peripheral portion, a portion of the first waist lapping section, extending on the side of the first longitudinal end edge from a first boundary line extending from a point on the first longitudinal end edge so as to be tangent to the stress relaxing structure is a waist lapping component force distributing region to which a component of the tensile force applied to the fastening means acts directly, a section of the oblique side edge of the ear part corresponding to the waist lapping component force distributing region is a first oblique side edge section, a portion of the first waist lapping section, extending on the side of the crotch lapping section from a second boundary line extending from a position at one end of the elastic leg fastening means on the side of the first waist lapping section so as to be tangent to the stress relaxing structure is a leg lapping component force distributing region to which a component of the fastening means acts directly, a section of the oblique side edge of the ear part corresponding to the leg lapping component force distributing portion is a second oblique side edge section, and the fastening means is attached to the ear part in a pulling section of the oblique side edge, overlapping at least part of the first oblique side edge section and part of the second oblique side edge section.

In a fourth aspect of the present invention, a disposable diaper comprises; an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge, respectively, a crotch lapping section extending between the first and the second waist lapping section; an elastic waist fastening means extended along the transverse edge of the absorbent part in the first waist lapping section; a pair of ear parts attached to the first waist lapping section of the absorbent part; and one fastening means attached to the oblique side edges of the ear parts, respectively. In this disposable diaper, the oblique side edges of the ear parts extend at an angle to the longitudinal center axis of the disposable diaper at a predetermined angle, the fastening means are attached to the ear parts so as to extend perpendicularly to the corresponding oblique side edges, respectively, each ear part has a stress relaxing structure, in which a tensile stress smaller than that which is induced in the peripheral portion of the ear part is induced, in a portion thereof other than the peripheral portion, a portion of the first waist lapping section, extending on the side of the first longitudinal end edge from a first boundary line extending from one end of the elastic waist fastening means on the side of the ear art so as to be tangent to a portion of the stress relaxing structure on the side of the same end of the elastic waist fastening means is a waist lapping component force distributing region in which a component of a tensile force applied to the fastening means acts directly on one end of the elastic waist fastening means, a section of the oblique side edge of the ear part corresponding to the waist lapping component force distributing region is a first oblique side edge section, a portion of the first waist lapping section, extending on the side of the crotch lapping section from a second boundary line extending from a point on the end edge of the ear part on the side of the crotch lapping section to the oblique side edge of the ear part so as to be tangent to the stress relaxing structure is a leg lapping component force distributing region in which a component of a tensile force applied to the fastening means acts directly on the end edge of the ear part, a section of the oblique side edge corresponding to the leg lapping component force distributing region is a second oblique side edge section, and the fastening means is attached to the ear part in a pulling section of the oblique side edge, overlapping at least part of the first oblique side edge section and part of the second oblique side edge section.

In a fifth aspect of the present invention, disposable diaper comprises; an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge respectively, a crotch lapping section extending between the first and the second waist lapping section; elastic leg fastening means extended along the opposite longitudinal side edges of the crotch lapping part; an elastic waist fastening means extended along the transverse edge of the absorbent part in the first waist lapping section; a pair of ear parts attached to the first waist lapping section of the absorbent part; and one fastening means attached to the oblique side edges of the ear parts, respectively. In this disposable diaper, the oblique side edges of the ear parts to which the fastening means are attached, respectively, are inclined at a predetermined angle to the longitudinal center axis of the disposable diaper, the fastening means are attached to the ear parts so as to extend perpendicularly to the corresponding oblique side edges, respectively, each ear part has a stress relaxing structure, in which a tensile stress smaller than that which is induced in the peripheral portion of the ear part is induced, in a portion thereof other than the peripheral portion, a portion of the first waist lapping section, extending on the side of the first longitudinal end edge from a first boundary line extending from a point on the first longitudinal end edge so as to be tangent to the stress relaxing structure is a waist lapping component force distributing region to which a component of a tensile force applied to the fastening means acts directly, a section of the oblique side edge of the ear part corresponding to the waist lapping component force distributing region is a first oblique side edge section, a portion of the first waist lapping section, extending on the side of the crotch lapping section from a second boundary line extending from a position at one end of the elastic leg fastening means on the side of the first waist lapping section so as to be tangent to the stress relaxing structure is a leg lapping component force distributing region in which a component of a tensile force applied to the fastening means acts directly on one end of the elastic leg fastening means, a section of the oblique side edge of the ear part corresponding to the leg lapping component force distributing region is a second oblique side edge section, and the fastening means is attached to the ear part in a pulling section of the oblique side edge, overlapping at least part of the first oblique side edge section and part of the second oblique side edge section.

The oblique side edges of the ear parts of the disposable diaper in accordance with the present invention are inclined at the predetermined angle to the longitudinal center axis of the disposable diaper, and the fastening means are disposed on the oblique side edges so as to extend substantially perpendicular to the oblique side edges, respectively; consequently, each fastening means is pulled invariably in a fixed direction relative to the corresponding oblique side edge of the ear part and appropriate tensile force is distributed to the portions of the absorbent part lapped around the legs.

When the inclination of the oblique side edge of the ear part, i.e., the angle as measured counterclockwise from a line parallel to the longitudinal center axis of the disposable diaper to the oblique side edge is in a range defined by: 0<<45 a major part of a tensile force applied to the fastening means can be distributed to the leg lapping section and a minor part of the same can be distributed to the waist lapping section, and a major part of a tensile force applied to the fastening means can be distributed to the waist lapping section and a minor portion of the same can be distributed to the leg lapping section when 45.

The stress relaxing structure of the ear part absorbs the tensile force applied thereto, and the peripheral portion of the ear part transmits the tensile force directly to the absorbent part, so that the tensile force applied to the fastening means can be effectively and directly applied to the waist lapping section and the leg lapping section of the absorbent part.

Attachment of the fastening means to the oblique side edge of the ear part in the pulling section overlapping at least part of the first oblique side edge section and the second oblique side edge section defined in positional connection with the absorbent part and the stress relaxing structure of the ear part ensures the application of the tensile force applied to the fastening means to part of the longitudinal end edge of the absorbent part on the side of the first waist lapping section or to part of the edge of the ear part on the side of the transverse center axis of the disposable diaper.

The tensile force that acts on part of the longitudinal end edge of the absorbent part on the side of the first waist lapping section or on part of the edge of the ear part on the side of the transverse center axis of the disposable diaper can be adjusted by adjusting the degree of overlap of the pulling section in which the fastening means is attached to the ear part with the first oblique side edge section or the second oblique side edge section. A major part of the tensile force applied to the fastening means is applied to the first waist lapping section when the degree of overlap of the pulling section with the first oblique side edge section is greater than that with the second oblique side edge section, and to a portion of the end edge of the ear part on the side of the transverse center axis of the disposable diaper when degree of overlap of the pulling section with the first oblique side edge section is smaller than that with the second oblique side edge section.

When the first oblique side edge section or the second oblique side edge section is defined in positional connection with the point where the line extending from the end of the elastic waist fastening means or the elastic leg fastening means so as to be tangent to the stress relaxing structure intersects the oblique side edge of the ear part, the application of the tensile force applied to the fastening means to the elastic waist fastening means and the elastic leg fastening means is ensured.

The above and other objects, features and advantages of the present invention will become more apparent from the following description taken in connection with the accompanying drawings.

DESCRIPTION OF THE PREFERRED EMBODIMENTS

Figure 1:
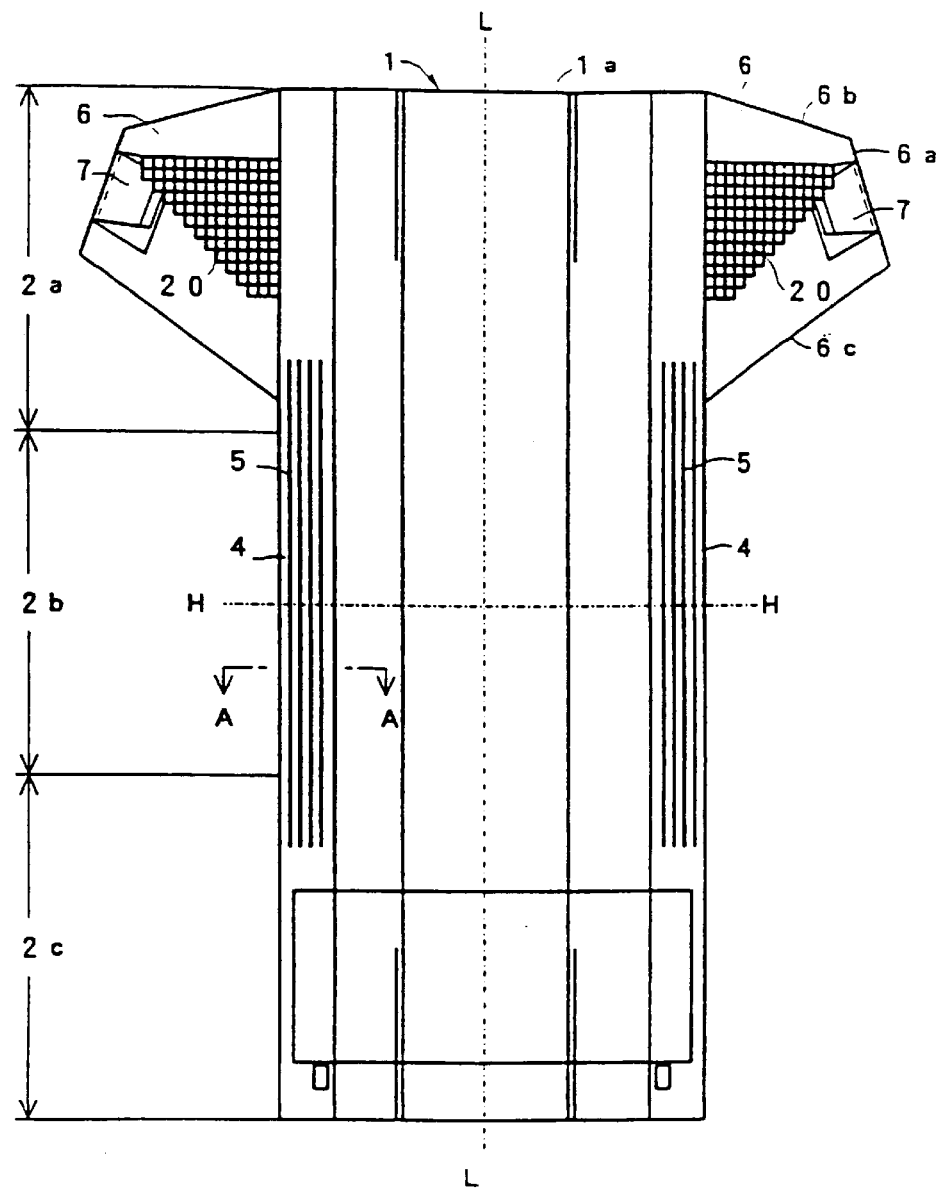
FIG. 1 is a development of a disposable diaper in accordance with the present invention.

In the following description, terms expressing positions, directions and the like indicate those as viewed in the drawings.

Referring to FIG. 1 a disposable diaper 1 in a first embodiment according to the present invention has a first waist lapping section 2a, a crotch lapping section 2b and a second waist lapping section 2c, and comprises an absorbent part formed substantially in a rectangular shape an hourglass shape, a T-shape, an asymmetric shape or such, side flaps 4 formed in the opposite side portions of the absorbent part 3, respectively, elastic members 5 longitudinally extended in the flaps 4 to provide the flaps 4 with elasticity, a pair of ear parts 6 projecting in opposite directions from the opposite side edges of the upper end portion of the first waist lapping section 2a of the absorbing part 3, respectively, and two fasteners 7 attached to the oblique side edges 6a of the ear parts 6, respectively.

Each ear part 6 has a slightly oblique upper edge 6b declining at a predetermined angle to the upper edge 1a parallel to the transverse center axis of the disposable diaper 1, an oblique side edge 6a extending obliquely downward from the outer end of the upper edge 6b, and an oblique lower edge 6c extending from the outer end of the oblique side edge 6a to the side edge of the absorbent part 3. The fastener 7 is attached to the ear part 6 so as to extend substantially perpendicularly to the oblique side edge 6a from the oblique side edge 6a. The inclination, i.e., the angle, as measured in a counterclockwise direction, between the oblique side edge 6a and a vertical line passing the intersection point of the upper side edge 6b and the oblique side edge 6a and parallel to the longitudinal center axis L–L' of the disposable diaper 1 meets an inequality: 0<<45. The tensile force distribution ratio, i.e., the ratio between a component of a tensile force applied to the fastener 7 distributed to a portion of the absorbent part 3 lapped around the waist and the waist lapping section and a component of the tension force distributed to a portion of the absorbent part 3 lapped around the leg, is dependent on the inclination. For example, it is possible to distribute a major component of the tensile force to the portion of the absorbent part 3 lapped around the leg and a minor component of the same to a portion of the absorbent part 3 lapped around the waist by properly determining the inclination.

Figure 2:
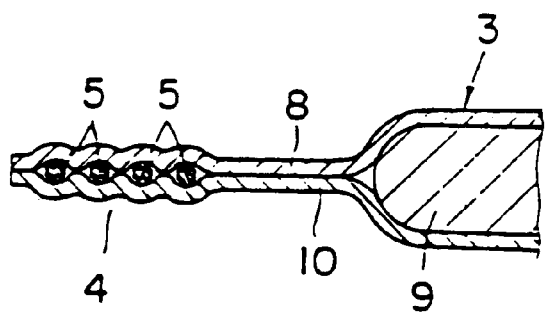
FIG. 2 is a fragmentary sectional view of a absorbent part of a disposable diaper in accordance with the present invention.

Referring to FIG. 2 showing a sectional view taken on line A—A in FIG. 1, the absorbent part 3 is formed by sandwiching an absorbent core 9 between a liquid-permeable top sheet 8 and a liquid-impermeable back sheet 10. The top sheet 8 and the back sheet 10 have a length and a width greater than those of the absorbent core 9. At least portions of the top sheet 8 and the back sheet 10, corresponding to the crotch lapping section 2b and extending outward beyond each longitudinal side edge of the absorbent core 9 form a side flap 4, and elastic members 5 are extended longitudinally in the side flap 4 to provide the side flap with elasticity. The absorbent core 9 is unirritative to the skin and capable of absorbing and holding liquid excrements including urine. Generally, the absorbent core 9 is formed of crushed wood pulp generally cold cotton pulp. The absorbent core 9 may be formed in any suitable shape and construction as occasion demands. The total absorption of the absorbent core 9 must correspond to a design charge and a desired use. The size and the absorbing ability of the absorbent core 9 are dependent on the wearer's age.

The back sheet 10 prevents wetting an article, such as a bed sheet or underwear, that comes into contact with the disposable diaper 1 with excrements absorbed and held by the absorbent core 9. The back sheet 10 is a film of a thermoplastic polymer, such as a polyethylene film, a polypropylene film or the like, or a film of a composite material, such as film-coated nonwoven fabric. Preferably, the back sheet 10 is an embossed thermoplastic film simulating fabric. The top sheet 8 is a porous foam sheet, a meshed foam sheet, a perforated plastic film or a woven or nonwoven fabric of a natural textile material, such as wood fibers or cotton fibers, a synthetic textile material, such as polyester fibers or polypropylene fibers, or a blended textile material, such as a blend of a natural textile material (or natural textile materials) and a synthetic textile material (or synthetic textile materials). Preferably, the top sheet 8 is formed of a hydrophobic material to separate the liquid absorbed by the absorbent core 9 from the wearer's skin.

Figure 3:
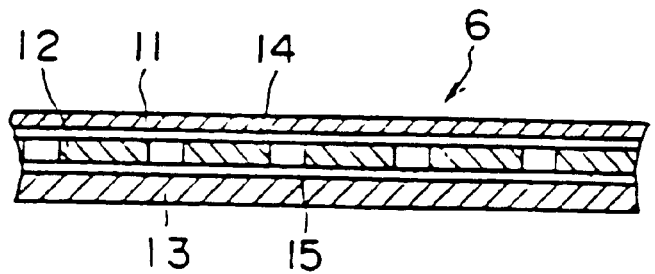
FIG. 3 is a fragmentary sectional view of a ear part.

The ear parts 6 having a substantially trapezoidal shape are joined to the opposite side edges of the first waist lapping section 2a of the rectangular absorbent part 3, respectively, by a known method, such as heat-sealing or adhesive bonding. The ear parts 6 may be formed integrally with the absorbent part 3 by projecting the respective upper side portions of the top sheet 8 and the back sheet 10 outward in lugs having the shape of the ear parts 6, and directly joining together the projecting lugs of the top sheet 8 and the back sheet 10. The absorbent part 3 and the ear parts 6 may be formed in an integral structure by cutting a laminated sheet formed by sandwiching a sheet between the top sheet 8 and the back sheet 10 in desired dimensions. Preferably, the ear parts 6 are formed by laminating a nonwoven fabric 11 of natural fibers, synthetic fibers or a blend of natural fibers and synthetic fibers, a thermoplastic film 13 of polyethylene or polypropylene, and a porous film 12 formed by a known process and sandwiched between the nonwoven fabric 11 and the thermoplastic film 13 by adhesive layers 14 and 15 as shown in FIG. 3. When each of the ear parts 6 is formed of an extension of the top sheet 8 and an extension of the back sheet 10, the nonwoven fabric 11 and the thermoplastic film 13 correspond to the extension of the top sheet 8 and the extension of the back sheet 10, respectively. The porous film 12 sandwiched between the nonwoven fabric 11 and the thermoplastic film 13 provides the ear parts 6 with firmness, which facilitates handling the ear parts 6 when putting the disposable diaper 1 on the wearer.

Figure 4:
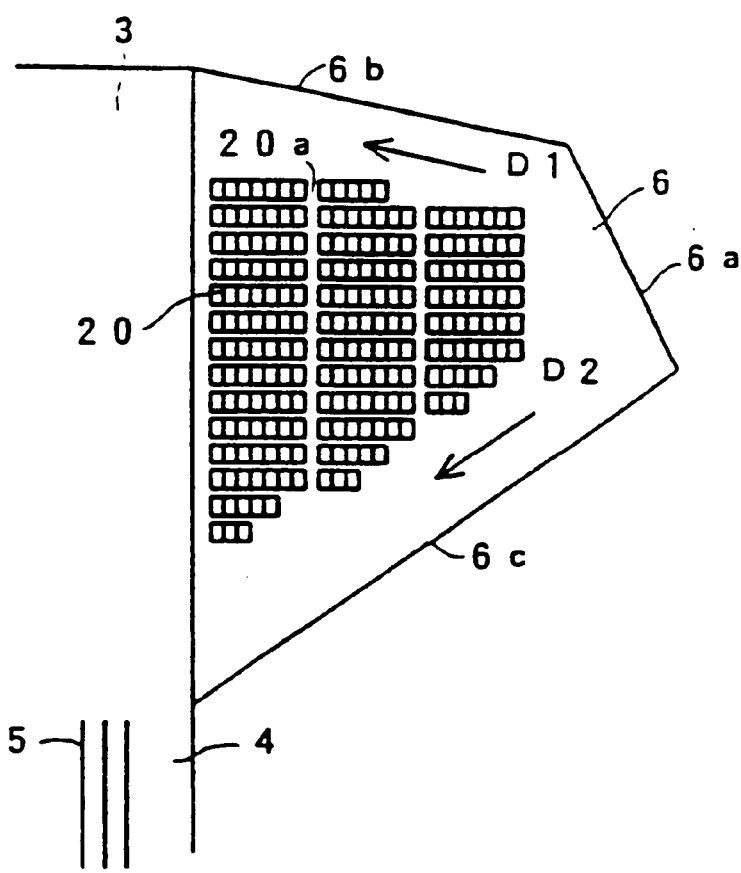
FIG. 4 is a plan view of a stress relaxing structure in a first example included in a disposable diaper in accordance with the present invention.
Figure 5:
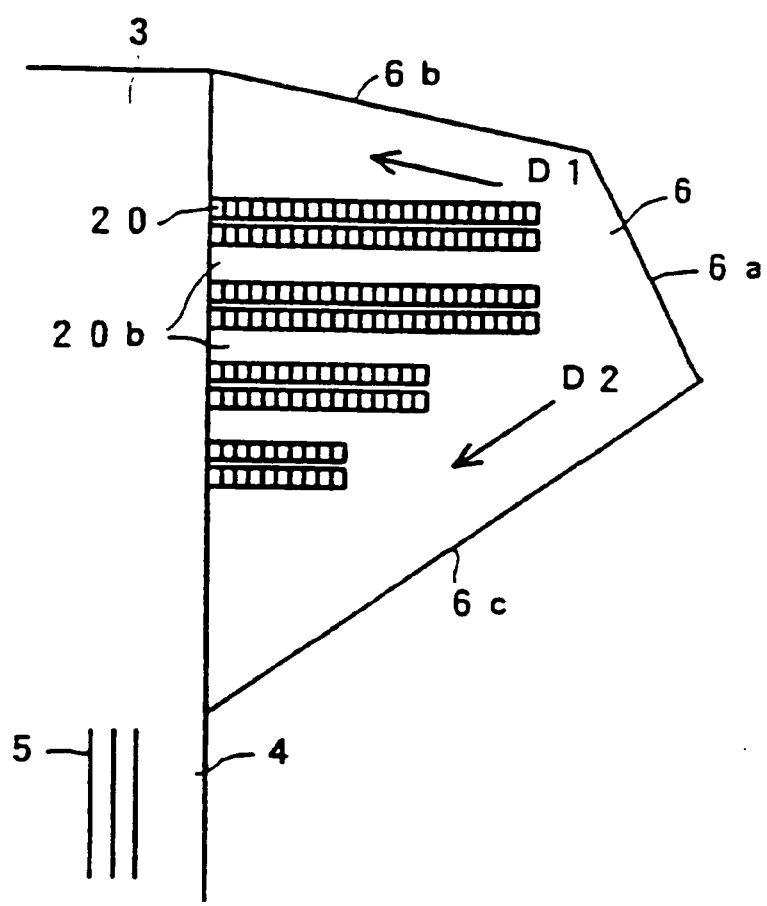
FIG. 5 is a stress relaxing structure in a second example included in a disposable diaper in accordance with the present invention.
Figure 6:
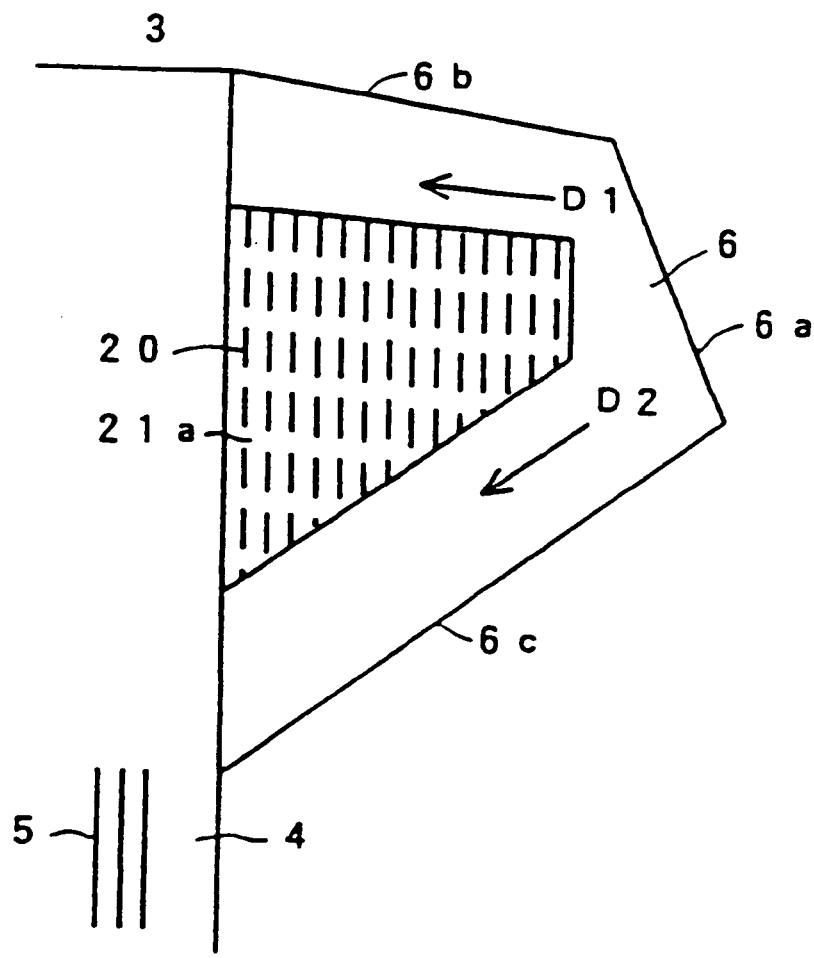
FIG. 6 is a stress relaxing structure in a third example included in a disposable diaper in accordance with the present invention.
Figure 7:
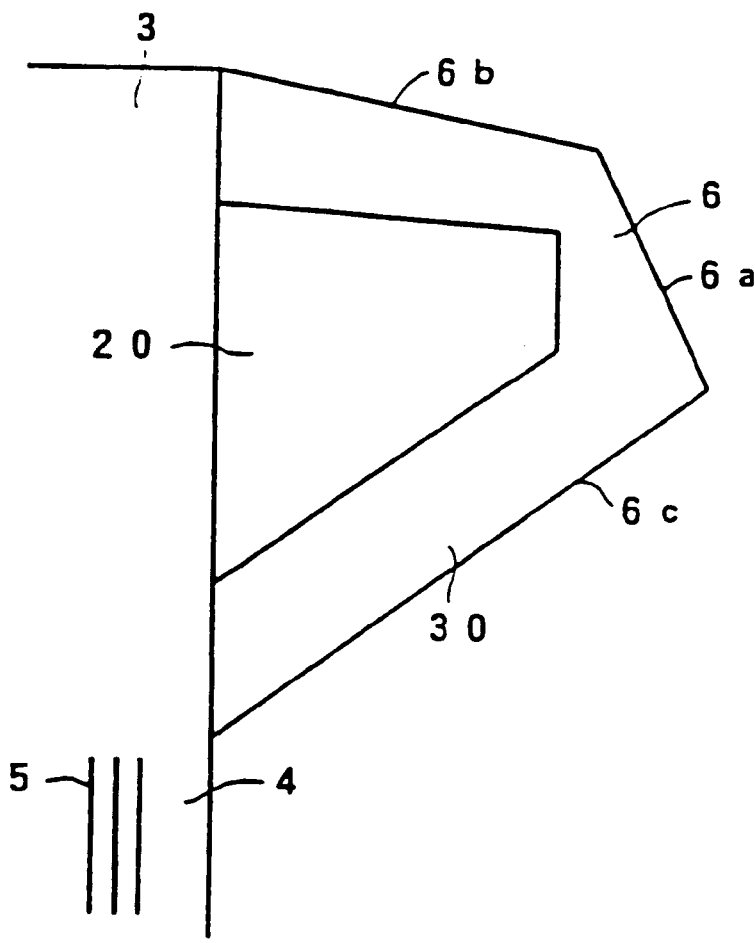
FIG. 7 is a stress relaxing structure in a fourthexample included in a disposable diaper in accordance with the present invention.

As shown in FIG. 6, the ear parts 6 have each a substantially trapezoidal stress relaxing structure 20 in their inner portions excluding the peripheral portions. The stress relaxing structure 20 may be formed in a substantially trapezoidal shape having longitudinal gaps 20a as shown in FIG. 4 or in a substantially trapezoidal shape having transverse gaps 20b as shown in FIG. 5. The stress relaxing structure 20 may be formed in any suitable shape other than a trapezoidal shape, such as a triangular shape, a rectangular shape, a shape of a part of an ellipse or a shape of a part of a circle, provided that the stress relaxing structure 20 has a function to relax stress. The stress relaxing structure 20 of the ear part 6 may be an aggregate of a plurality of longitudinal slits 21a formed in the laminated sheet forming the ear part 6 as shown in FIG. 6. The stress relaxing structure 20 may be a single slit 21a provided that the single slit 21a is capable of intercepting the transmission of a tensile force applied to the ear part 6 to the absorbent part 3. As shown in FIG. 7, the ear part 6 may be formed in an elastic structure, and a strip of an unstretchable film or an unstretchable strand 30 may be attached to a peripheral portion of the elastic structure excluding an inner trapezoidal elastic portion corresponding to the stress relaxing structure 20 to use the inner trapezoidal elastic portion as the stress relaxing structure 20.

When a tensile force is applied to the ear part 6, a tensile stress induced in the stress relaxing structure 20 is smaller than that which is induced in the peripheral portion of the ear part 6 surrounding the stress relaxing structure 20. Tensile stress is a resistive force developed by a material bearing a tensile load. Therefore, "a structure having a small tensile stress" is a structure yielding to and easily stretchable by a comparatively small tensile force. Structures expressed by the term "stress relaxing structure" include a vacancy formed in the ear part 6 and virtually serving as a stress relaxing structure 20.

Figure 8:
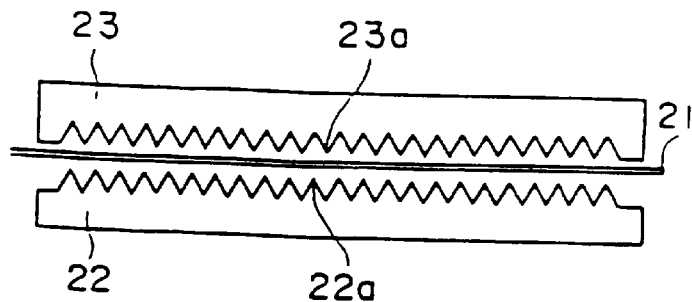
FIG. 8 is a typical side view of assistance in explaining a stress relaxing structure forming device.
Figure 9:
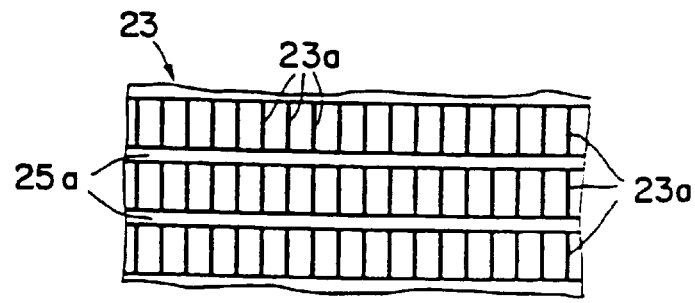
FIG. 9 is a plan view of a forming plate of the stress relaxing structure forming device.
Figure 10:
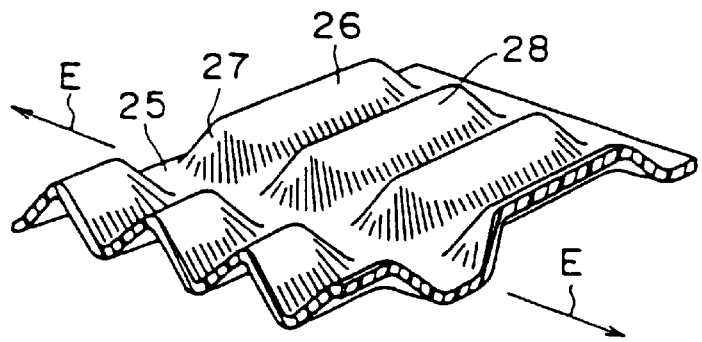
FIG. 10 is a fragmentary perspective view of a stress relaxing structure formed by the stress relaxing structure forming device of FIG. 8.

Preferably, the stress relaxing structure 20 is formed by the following method. As shown in FIG. 8, a sheet 21 to form the ear part 6 is compressed between a plate 22 provided with a plurality of ridges 22a in an area of the inner surface thereof corresponding to the stress relaxing structure 20, and a plate 23 provided with a plurality of ridges 23a in an area of the inner surface thereof corresponding to the stress relaxing structure 20. As shown in FIG. 9, narrow grooves 25a are formed across the plurality of ridges 23a of the plate 23. The plurality of ridges 22a of the plate 22 are continuous and not interrupted. As shown in FIG. 10, the stress relaxing structure 20 formed by thus compressing the sheet 21 between the plates 22 and 23 has a plurality of undeformed sections 25, a plurality of permanently deformed sections 26, and transitional sections 27 between the undeformed sections 25 and the permanently deformed sections 26. Ridges 28 are formed in the permanently deformed sections 26. The undeformed sections 25 are defined by the narrow grooves 25a of the plate 23 and the corresponding portions of the ridges 22a of the plate 22, and the permanently deformed sections 26 are defined by the respective ridges 22a and 23a of the plate 22 and the plate 23.

Figure 11:
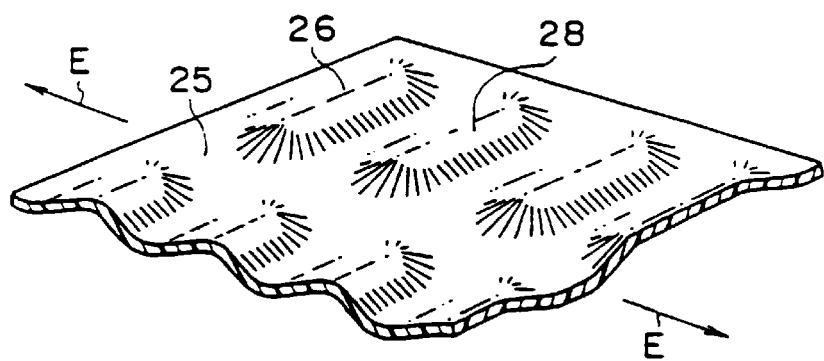
FIG. 11 is a fragmentary perspective view of a formed intermediate film shown in FIG. 10, in a half stretched state.
Figure 12:
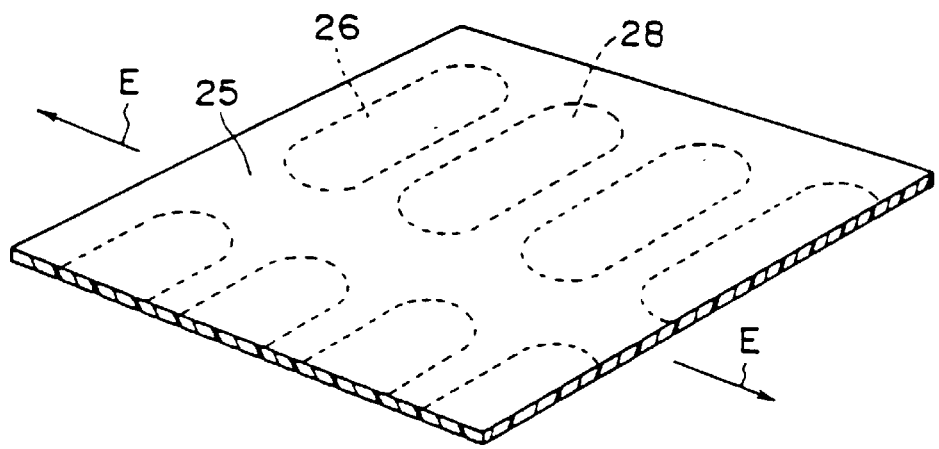
FIG. 12 is a fragmentary perspective view of the formed intermediate film shown in FIG. 10 in a fully stretched state.

When the ear part 6 is tensioned by forces acting in the directions of the arrows E as shown in FIG. 10, the undeformed sections 25 are plastically stretched to some extent as shown in FIG. 11 and, as the undeformed sections 25 are further stretched, the ridges 28 of the permanently deformed sections 26 are flattened as shown in FIG. 12 and the ear part 6 cannot be stretched any further. When the sheet 21 having such characteristics is a laminated sheet, at least one of the component layer of the sheet 21 is formed of a stretchable film, such as a polyolefin film, a low-density linear polyethylene film, a low-density polyethylene film, a high-density polyethylene film or a polypropylene film.

The stress relaxing structure 20 that can be stretched by a small tensile force is thus formed in the sheet 21 forming the ear part 6. Since the periphery of the sheet 21 surrounding the stress relaxing structure 20 is unprocessed, the periphery of the sheet 21 does not yield to tension when the sheet 21 is tensioned or the periphery is harder to stretch than the stress relaxing structure 20. When tensioned, the stress relaxing structure 20 yields to the tensile force to absorb the tensile force and does not cause the peripheral portion of the ear part 6 to shrink.

The sheet 21 forming the ear part 6 may be formed of a somewhat stretchable material. When formed of such a somewhat stretchable material, the stress relaxing structure 20 can be formed in the sheet 21 by the aforesaid process. In either case, the stress relaxing structure 20 can be stretched by a tensile force smaller than that necessary for stretching the peripheral portion of the ear part 6.

Figure 13:
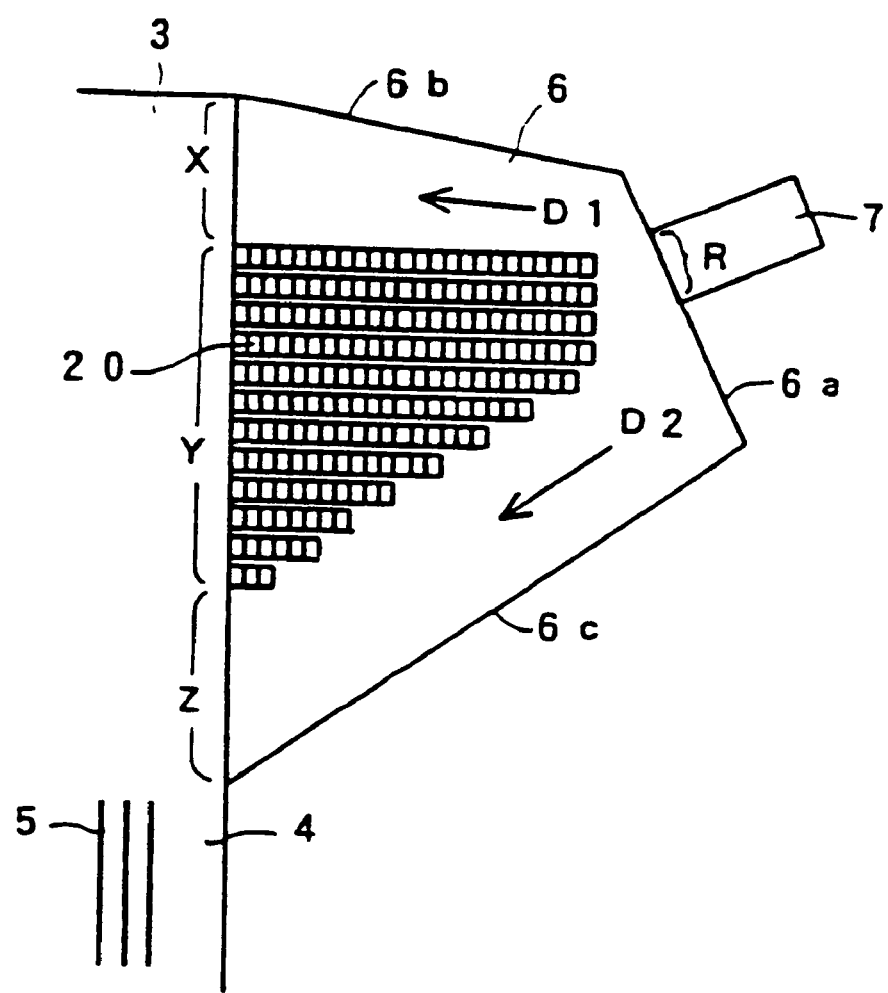
FIG. 13 is a fragmentary development of a disposable diaper in accordance with the present invention, for assistance in explaining the distribution of a tensile force applied to a fastener at a predetermined distribution ratio.

As shown in FIG. 13, when a tensile force D is applied to the fastener 7 in a direction perpendicular to the oblique side edge 6*a* of the ear part 6, the stress relaxing structure 20 of the ear part 6 serves to divide the tensile force D into a component tensile force D1 acting on the waist lapping portion and a component tensile force D2 acting on the leg lapping portion. That is, since a tensile force greater than that necessary for stretching the stress relaxing structure 20 must be applied to the peripheral portions of the ear part 6 to stretch the peripheral portion, most part of the tensile force applied to the fastener 7 is divided into the component tensile forces D1 and D2, and the component tensile forces D1 and D2 act directly on regions X and Z of the absorbent part 3, respectively. Even if part of the tensile force D acts on the stress relaxing structure 20, the stress relaxing structure 20 is not stretched in a extreme state as shown in FIG. 12 because the stress relaxing structure 20 can be stretched by a comparatively small tensile force and the peripheral portion surrounding the stress relaxing structure 20 cannot be virtually stretched. Thus, the stretchable stress relaxing structure 20 absorbs the tensile force that acts thereon and, consequently, any tensile force is not transmitted directly to a region Y of the absorbent part 3. Thus the tensile force D applied to the fastener 7 is divided into the component tensile force D1 acting on the waist lapping portion of the absorbent part 3 and the component tensile force D2 acting on the leg lapping portion of the absorbent part 3 to fasten the absorbent part 3 around the waist and the leg.

Figure 14:
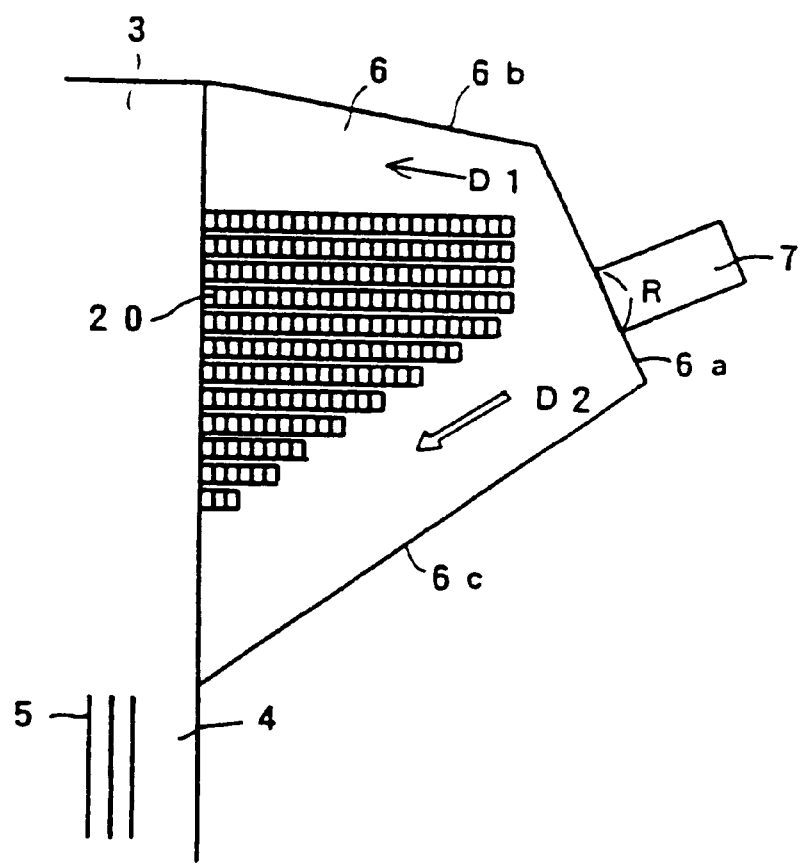
FIG. 14 is a fragmentary development of a disposable diaper in accordance with the present invention, for assistance in explaining the distribution of a major part and a minor part of a tensile force applied to a fastener to a waist lapping section and a leg lapping section, respectively, of the disposable diaper.
Figure 15:
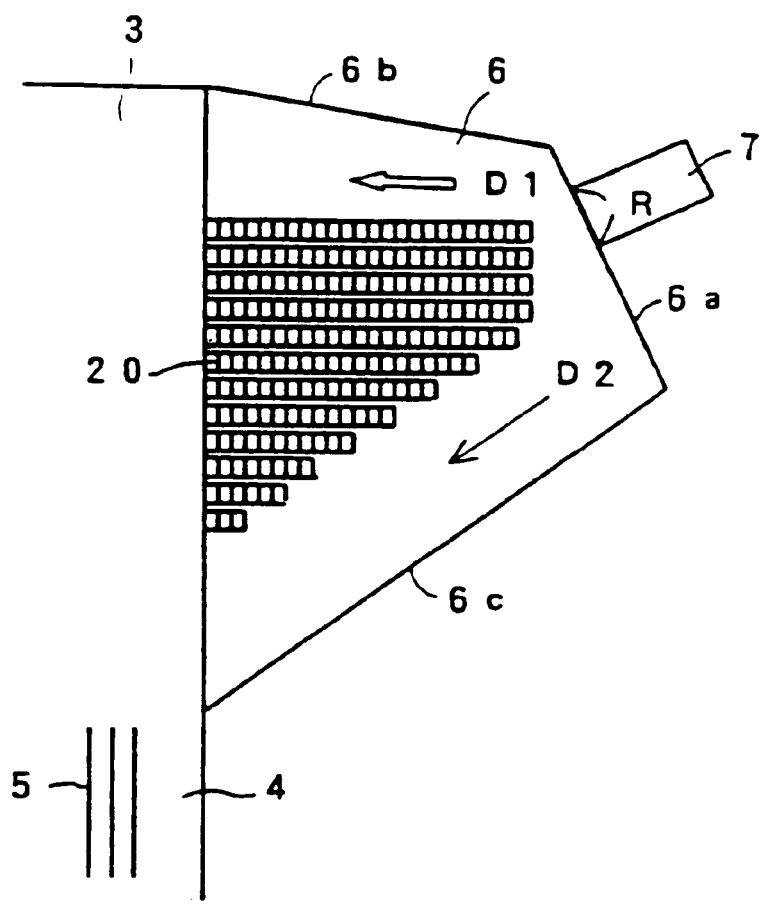
FIG. 15 is a fragmentary development of a disposable diaper in accordance with the present invention, for assistance in explaining the distribution of a minor part and a major part of a tensile force applied to a fastener to a waist lapping section and a leg lapping section, respectively, of the disposable diaper.

The fastener 7 is attached to the oblique side edge 6*a* of the ear part 6 so as to extend perpendicularly to the oblique side edge 6*a*, and the fastener 7 is pulled in a direction perpendicular to the oblique side edge 6*a*. Since the fastener 7 is pulled necessarily in a direction perpendicular to the oblique side edge 6*a* of the ear part 6, the direction in which the fastener 7 is pulled with respect to the absorbent part 3 is dependent on the inclination of the oblique side edge 6*a*, which may be varied in the range of $0 << 45$. That is, since the fastener 7 is pulled in a fixed direction with respect to the oblique side edge 6*a*, the difference between the component tensile forces D1 and D2 is not very large when the inclination of the oblique side edge 6*a* is small, and the ratio of the component tensile force D2 to the component tensile force D1 increases with the increase of the inclination of the oblique side edge 6*a*. The division of the tensile force D applied to the fastener 7 into the component tensile forces D1 and D2 cam be adjusted by adjusting the position of a pulling section R where the fastener 7 is attached to the oblique side edge 6*a* of the ear part 6. When the pulling section R corresponds substantially to the middle of the side edge of the stress relaxing structure 20 as shown in FIG. 13, the tensile force D applied to the fastener 7 in the direction of the arrow is divided into the component tensile forces D1 and D2, and the component tensile force D2 that acts around the leg is greater than the component tensile force D1 that acts around the waist by a predetermined value. When the pulling section R is at a position shown in FIG. 14 below the position of the pulling section R shown in FIG. 13, the tensile force D applied to the fastener 7 in the direction of the arrow is divided into the component tensile forces D1 and D2, the component tensile force D1 that acts around the waist is comparatively large and the component tensile force D2 that acts around the leg is comparatively small.

Figure 16:
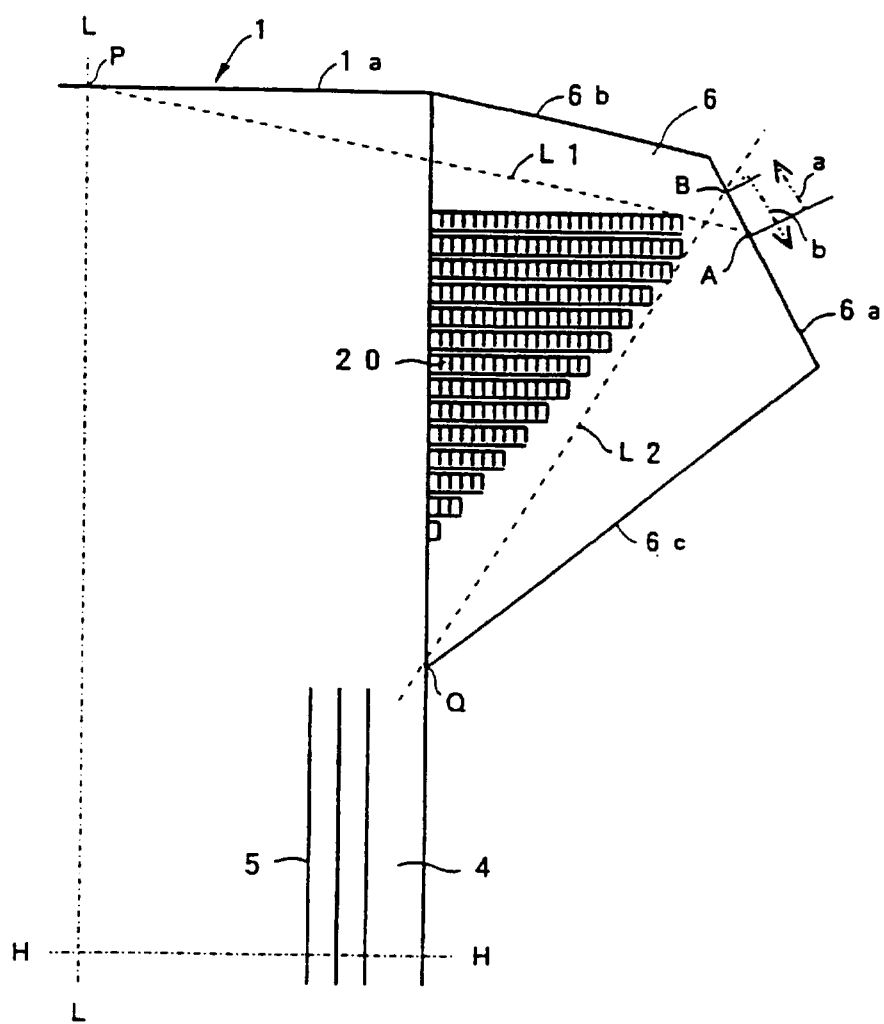
FIG. 16 is a fragmentary development of assistance in explaining a first oblique side edge section a and a second oblique side edge section b.

The position of the pulling section R and the positional relation between the same and other parts to distribute the tensile force applied to the fastener 7 surely to desired portions of the absorbent part 3 will be described below. The position of the pulling section R for the fastener 7 on the oblique side edge 6*a* is determined by construction shown in FIG. 16. The position of the pulling section R is important for effectively and directly distributing a tensile force applied to the fastener 7 to a desired waist lapping portion and a desired leg lapping portion of the disposable diaper 1. Referring to FIG. 16, a line L–L' indicates the longitudinal center axis of the disposable diaper 1 and a line H–H' indicates the transverse center axis of the disposable diaper 1 perpendicular to the longitudinal center axis L–L'. Indicated at P is the intersection point of the longitudinal center axis L–L' and the upper edge 1*a* of the first waist lapping section 2*a*, at Q is the intersection point of the lower side edge 6*c* of the ear part 6 on the side of the transverse center line H–H' and the side flap 4, at L1 is a line extending from the intersection point P so as to be tangent to a point on the stress relaxing structure 20 on the side of the upper edge 1*a*, at L2 is a line extending from the intersection point Q so as to be tangent to a point on the stress relaxing structure 20 on the side of the transverse center axis H–H', at A is the intersection point of the line L1 and the oblique side edge 6*a*, and at B is the intersection point of the line L2 and the oblique side edge 6*a*. A first oblique side edge section a extends on the side of the upper edge 1*a* from the intersection point A, and a second oblique side edge section b extends on the side of the transverse center axis H–H' from the intersection point B.

Figure 17:
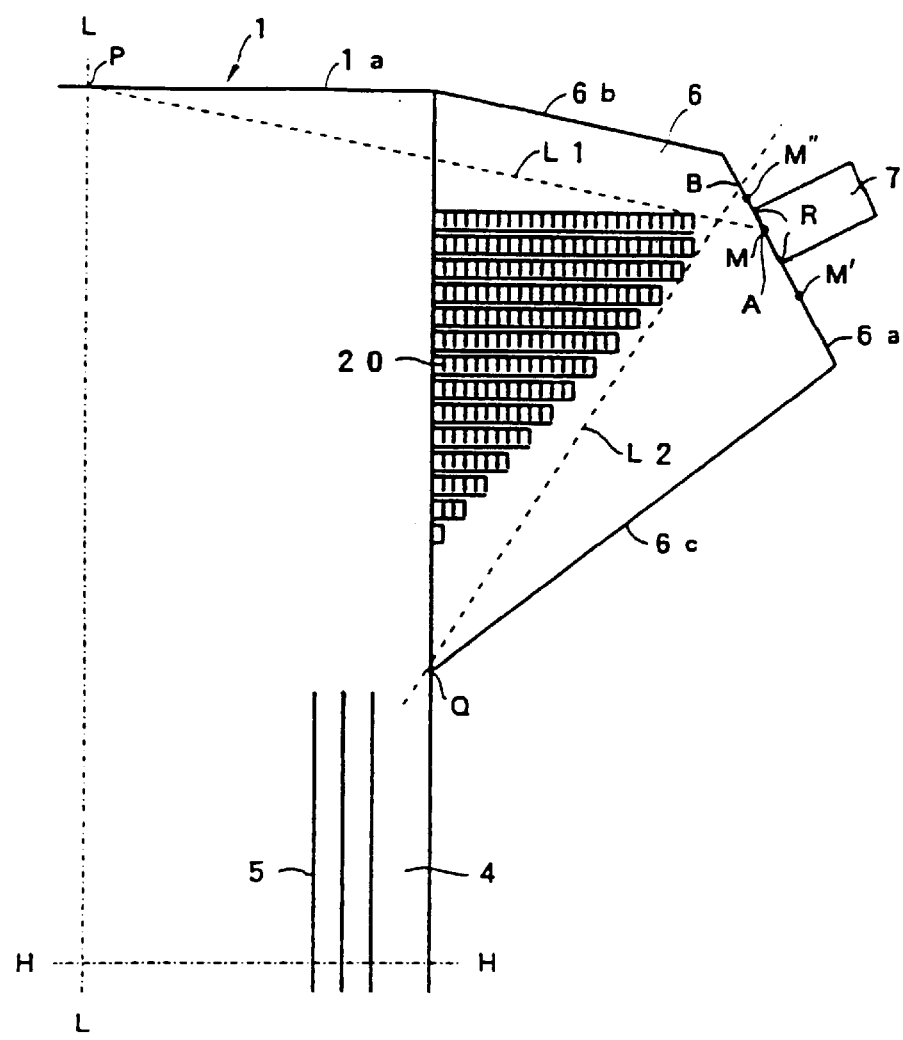
FIG. 17 is a fragmentary development of assistance in explaining the dependence of the distribution of a tensile force on the position of a fastener on an ear part.
Figure 18:
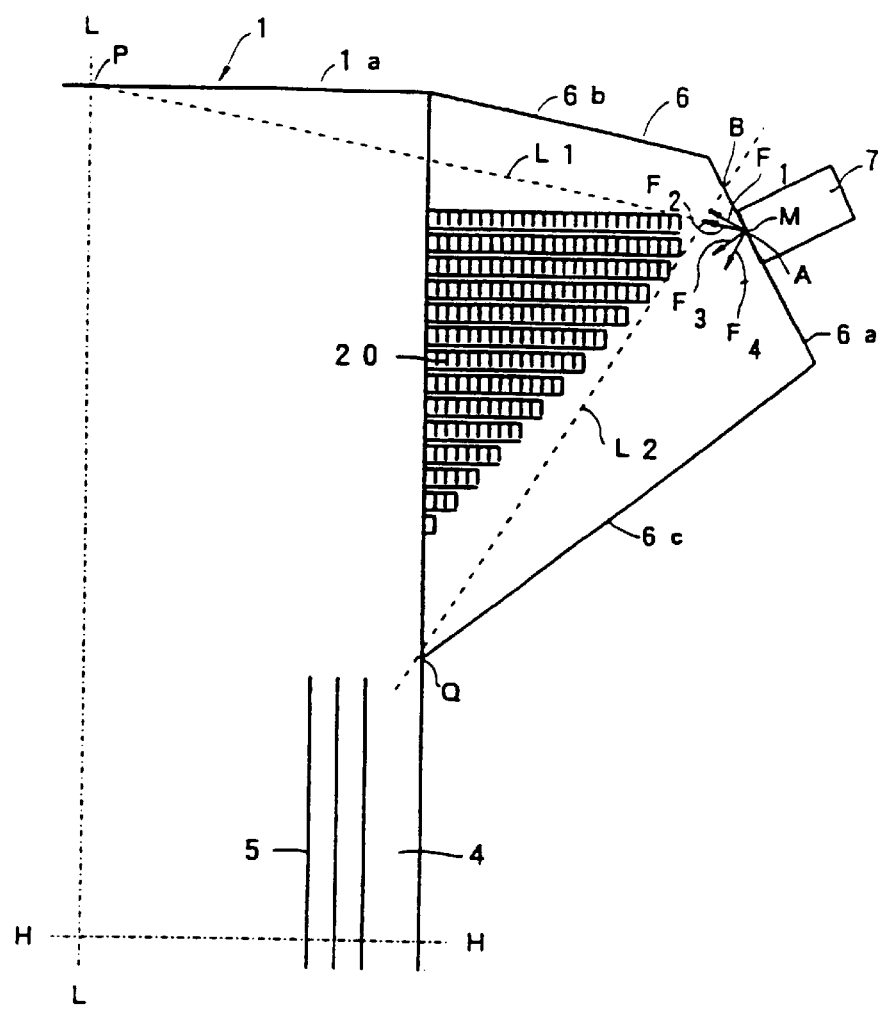
FIG. 18 is a fragmentary development of assistance in explaining the distribution of a tensile force applied to a fastener.

A tensile force D applied to the oblique side edge 6*a* by the fastener 7 is distributed in the ear part 6 as shown in FIG. 17. In FIG. 17, a point M of action of the tensile force applied to the fastener 7 is in the pulling section R in which the fastener 7 is attached to the oblique side edge 6*a* and coincides with the intersection point A in this example. When part of a tensile force applied to the fastener 7 acts on the oblique side edge 6*a* at the point M of action, the part of the tensile force is decomposed into representative component forces F1, F2, F3 and F4 as shown in FIG. 18. The component force F1 is directed toward the upper edge 1*a* and not directly toward the intersection point P. Therefore, the component force F1 does not act directly on the intersection point P. The direction of the component force F2 is aligned with the line L1 and hence the component force F2 acts directly on the intersection point P. The component force F3 is directed toward the stress relaxing structure 20 and tends to stretch the stress relaxing construction 20. However, since the stress relaxing structure 20 absorbs the force applied thereto, the component force F3 is not transmitted to the region Y of the absorbent part 3 shown in FIG. 13. The component force F4 is directed toward the intersection point Q and acts directly on the absorbent part 3 at the intersection point Q.

If the point M of action in the pulling section R in which the fastener 7 is attached to the oblique side edge 6a is on the side of the transverse center axis H–H' with respect to the intersection point A, i.e., at a point M' outside the first oblique side edge section a (FIG. 16), the component force F2 directed from the point M' toward the intersection point P is absorbed by the stress relaxing structure 20 and is ineffective. Therefore, no component force acts directly on the intersection point P if the point M of action of the tensile force applied to the fastener 7 on the oblique side edge 6a is at the point M'. If the point M action is shifted to a point M" on the side of the upper edge 1a with respect to the intersection point A shown in FIG. 17, i.e., if the point M of action is in the first oblique side edge section a, some component force acts directly on the intersection point P.

As is obvious from the foregoing explanation, the line L1 is a boundary line between positions for the point M of action that enables the direct action of a component force of the tensile force applied to the fastener 7 on the intersection point P and those for the point M of action that disables the direct action of the component force on the intersection point P. When the point M of action at which the tensile force applied to the fastener 7 acts on the ear part 6 is in the first oblique side edge section a, at least part of the tensile force applied to the point M of action is able to act directly on the intersection point P. The line L2 drawn in connection with the intersection point Q is a boundary line between positions for the point M of action that enables the direct action of a component force of the tensile force applied to the fastener 7 on the intersection point Q. When the point M of action at which the tensile force applied to the fastener 7 acts on the ear part 6 is in the second oblique side edge section b, at least part of the tensile force applied to the point M of action is able to act directly on the intersection point Q. Accordingly, part of the tensile force applied to the fastener 7 can be applied directly on the desired points P and Q on the absorbent part 3 when the pulling section R in which the fastener 7 is attached to the oblique side edge 6a of the ear part 6 overlaps part of the first oblique side edge section a defined by the line L1 and part of the second oblique side edge section b defined by the line L2. Since the intersection point P is on the longitudinal center line L–L' of the disposable diaper 1, the waist lapping portion of the disposable diaper 1 can be firmly fastened around the waist by applying tensile forces to the two ear parts 6, when part of each of the tensile forces can be applied directly to the intersection point P. When part of the tensile force applied to each fastener 7 can be directly applied to the intersection point Q, the leg lapping portion of the absorbent part 3 can be firmly fastened around the leg. Since the fastener 7 is attached to the oblique side edge 6a of the ear part 6 in the pulling section R so as to extend perpendicularly to the oblique side edge 6a, the direction in which a tensile force is applied to the fastener 7 with respect to the absorbent part 3 is dependent on the inclination of the oblique side edge 6a and the tensile force applied to each fastener 7 can be distributed in directions toward the waist lapping portion and the leg lapping portion at a predetermined distribution ratio.

Figure 19:
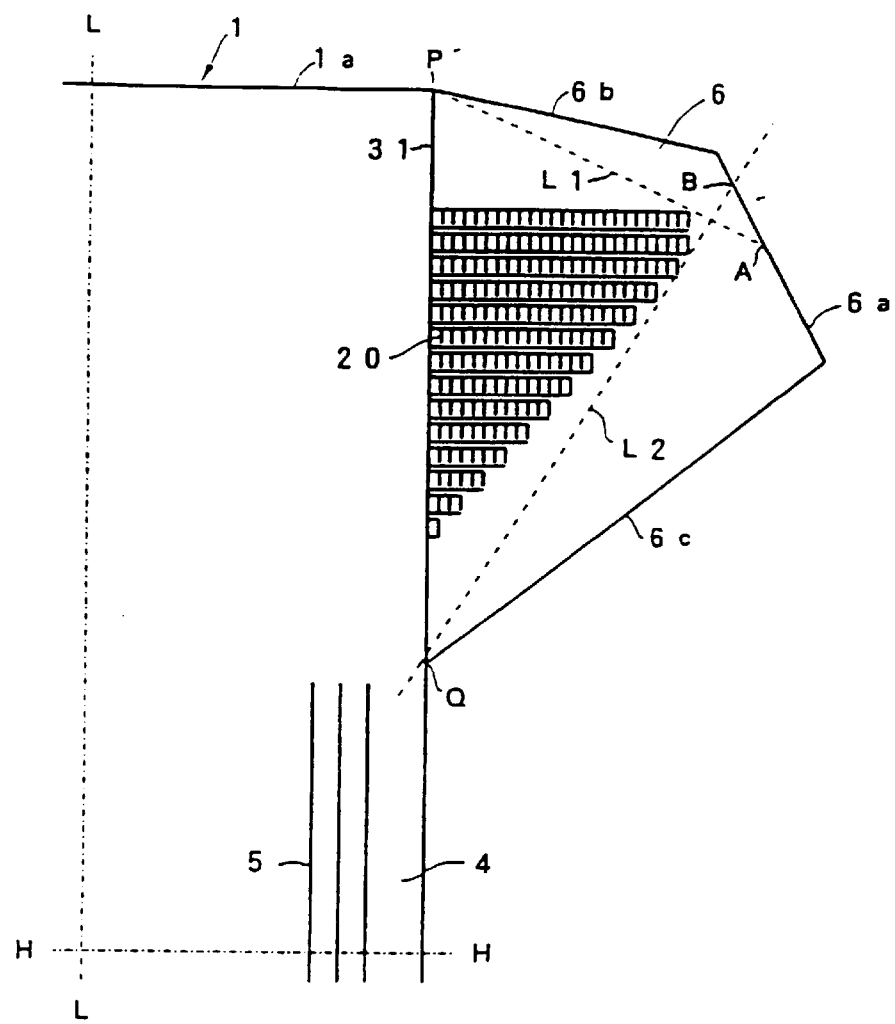
FIG. 19 is a fragmentary development of assistance in explaining a method of determining a first oblique side edge section.
Figure 20:
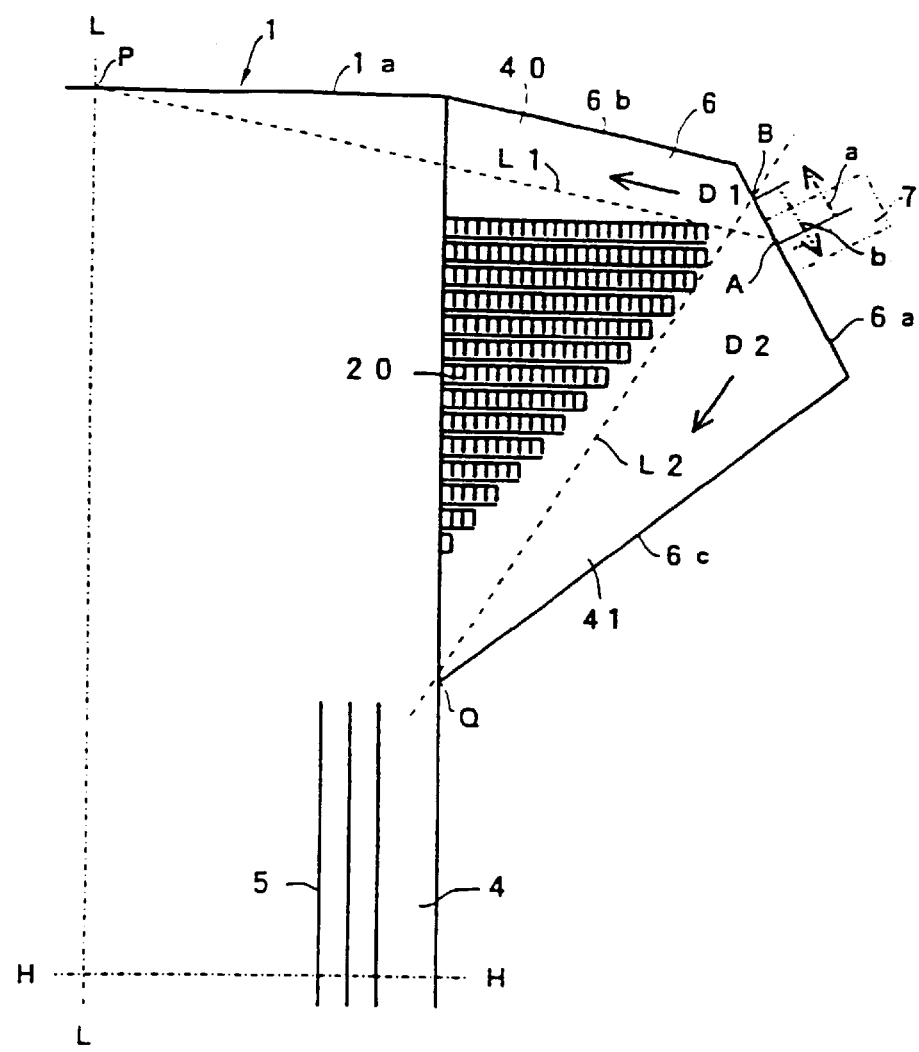
FIG. 20 is a fragmentary development of assistance in explaining another method of determining a first oblique side edge section.

As shown in FIG. 19, in a disposable diaper 1 in a second embodiment according to the present invention, a line L1 is extended from the intersection point P', which corresponds to the intersection point P in the first embodiment, of the upper edge 1a of an absorbent part 3 and the side edge 31 of the absorbent part 3 parallel to the longitudinal center axis L–L' of the disposable diaper 1 so as to be tangent to a stress relaxing structure 20, a line L2 is extended from the intersection point Q of the lower end of an ear part 6 and a flap 4 extended along the side edge 31 of the absorbent part 3, the line L1 intersects the oblique side edge 6a of the ear part 6 at an intersection point A, which corresponds to the intersection point A in the first embodiment, and the line L2 intersects the oblique side edge 6a at an intersection point B, which corresponds to the intersection point B in the first embodiment.

The respective magnitudes of a component tensile force D1 for fastening the waist lapping portion of the absorbent part 3 around the waist and a component tensile force D2 for fastening the leg lapping portion of the absorbent part 3 around the leg are determined by adjusting the ratio of the size of a portion of the pulling section R, in which a fastener 7 is attached to the oblique side edge 6a, overlapping the first oblique side edge section a to the size of the pulling section R, and the ratio of the size of a portion of the pulling section R overlapping the second oblique side edge section b to the size of the pulling section R. The greater the portion of the pulling section R, overlapping the first oblique side edge section a, the greater is the ratio of the component tensile force D1 that acts on the intersection point P' to the tensile force applied to the fastener 7. An area defined by the line L1, the upper side edge 6b of the ear part 6 and the oblique side edge 6a of the ear part 6 is a waist lapping portion fastening component force distributing area 40, and a portion of the oblique side edge 6a associated with the waist lapping portion fastening component force distributing area 40 is a first oblique side edge section a. As long as part of the pulling section R in which the fastener 7 is attached to the oblique side edge 6a overlaps the first oblique side edge section a, a component tensile force of the tensile force applied to the fastener 7 acts directly on the intersection point P'. The greater the portion of the pulling section R, overlapping the first oblique side edge section a, the greater is the component tensile force D1 distributed to the waist lapping portion fastening component force distributing area 40.

On the other hand, the greater the portion of the pulling section R, overlapping the second oblique side edge section b, the greater is the component tensile force D2 that acts directly on the intersection point Q. An area defined by the line L2, the lower side edge 6c of the ear part 6 and the oblique side edge 6a of the ear part 6 is a leg lapping portion fastening component force distributing area 41, and a portion of the oblique side edge 6a associated with the leg lapping portion fastening component force distributing area 41 is a second oblique side edge section b. As long as part of the pulling section R overlaps the second oblique side edge section b, a component tensile force of the tensile force applied to the fastener 7 acts directly on the intersection point Q. The greater the portion of the pulling section R, overlapping the second oblique side edge section b, the greater is the component tensile force D2 distributed to the leg lapping portion fastening component force distributing area 41.

The ratio between the component tensile force D1 distributed to the waist lapping portion fastening component force distributing area 40 and the component tensile force D2 distributed to the leg lapping portion fastening component force distributing area 41 can be adjusted by adjusting the ratio of the size of a portion of the pulling section R, in which a fastener 7 is attached to the oblique side edge 6a, overlapping the first oblique side edge section a to the size of the pulling section R, and the ratio of the size of a portion of the pulling section R overlapping the second oblique side edge section b to the size of the pulling section R. When the pulling section R, in which the fastener 7 is attached to the oblique side edge 6a, overlaps the first oblique side edge section a entirely and overlaps the second oblique side edge section b partly, a major part of the tensile force applied to the fastener 7 is distributed to the waist lapping portion fastening component force distributing area 40. When the pulling section R overlaps the second oblique side edge section b entirely and overlaps the first oblique side edge section a partly, a major part of the tensile force applied to the fastener 7 is distributed to the leg lapping portion fastening component force distributing area 41. The pulling section R in which the fastener 7 is attached to the oblique side edge 6a need not necessarily be included in either the first oblique side edge section a or the second oblique side edge section b, provided that pulling section R overlaps the first oblique side edge section a and the second oblique side edge section b at different overlapping ratios, respectively.

The fastener 7 is attached to the oblique side edge 6a in the pulling section R so as to extend perpendicularly to the oblique side edge 6a, so that the tensile force applied to the fastener 7 acts in a direction oblique to the longitudinal center axis L–L' of the disposable diaper 1, and the tensile forces applied to the two fasteners 7 attached to the ear parts 6 can be distributed to the waist lapping portion and the leg lapping portions at a predetermined distribution ratio.

Figure 21:
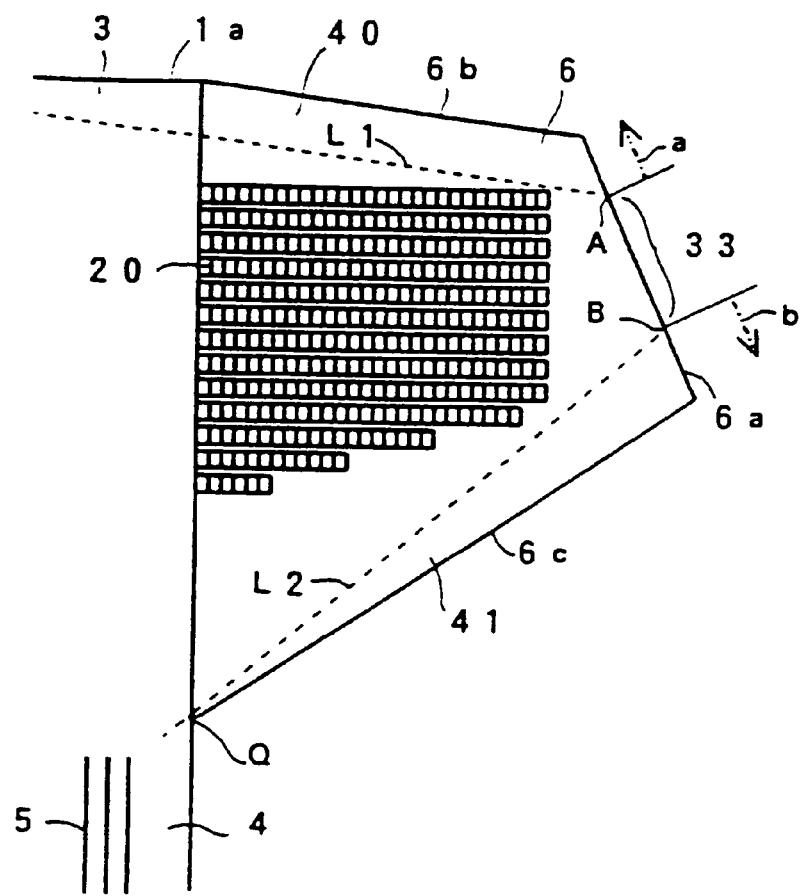
FIG. 21 is a fragmentary development of assistance in explaining the positional relation of a first oblique side edge section a and a second oblique side edge section b with a stress relaxing structure formed in a disposable diaper in accordance with the present invention.
Figure 22:
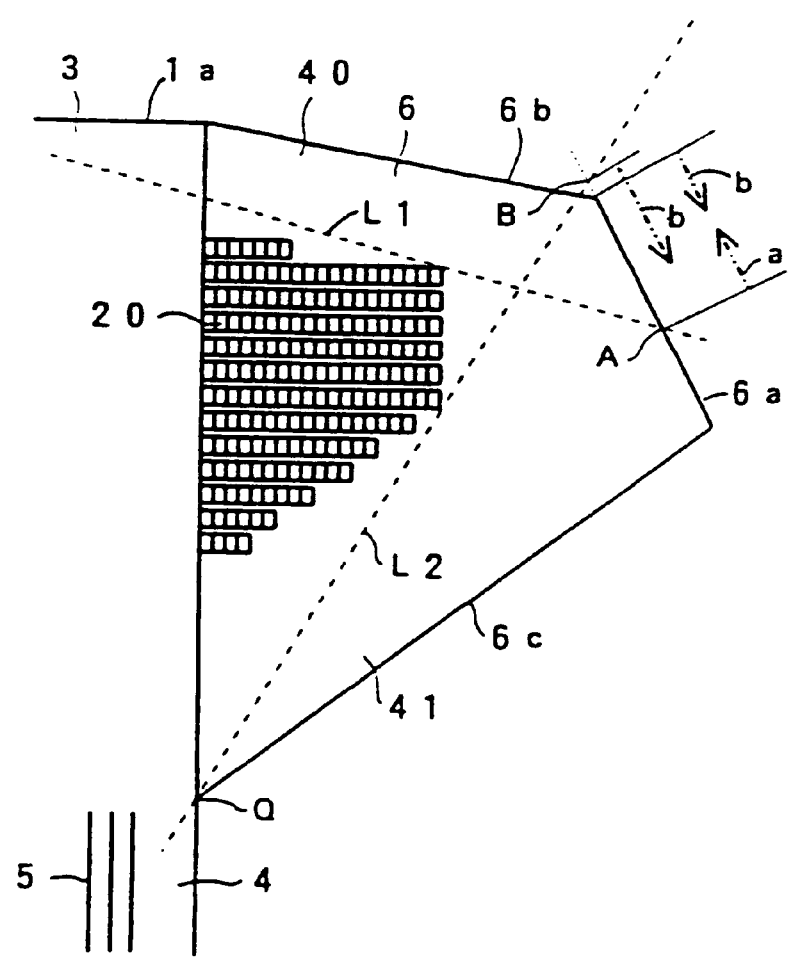
FIG. 22 is a fragmentary development of assistance in explaining the positional relation of a first oblique side edge section a and a second oblique side edge section b with a stress relaxing structure formed in a disposable diaper in accordance with the present invention.

FIGS. 21 and 22 show the dependence of the relation between the first oblique side edge section a and the second oblique side edge section b on the position of a stress relaxing structure 20 in an ear part 6 in a disposable diaper 1 in a third embodiment according to the present invention. Referring to FIG. 21, the stress relaxing structure 20 has a shape resembling a rectangle, which is different from the shape of the stress relaxing structure 20 shown in FIG. 16. In the third embodiment, the line L1 extending from the intersection point P so as to be tangent to the stress relaxing structure 20 and the line L2 extending from the intersection point Q so as to be tangent to the stress relaxing structure 20 do not intersect each other within the ear part 6. The lines L1 and L2 intersect the oblique side edge 6a at intersection points A and B, respectively. A first oblique side edge section a extends on the side of the upper edge 1a of an absorbent part 3 from the intersection point A, a second oblique side edge section b extends on the side of the transverse center axis H–H' of the absorbent part 3 from the intersection point B, and a neutral section 33 connected with neither the waist lapping portion fastening component force distributing area 40 nor the leg portion fastening component force distributing area 41 is formed between the first oblique side edge section a and the second oblique side edge section b. The pulling section R in which a fastener 7 is attached to the oblique side edge 6a must extend across the neutral section 33 and overlap the oblique side edge sections a and b partly to concentrate the component forces of the tensile force applied to the fastener 7 directly on the waist lapping portion and the leg lapping portion; that is, the component forces of the tensile force applied to the fastener 7 can be directly concentrated on desired portions by determining the position of the pulling section R so that the pulling section R overlap the oblique side edge sections a and b partly.

In a disposable diaper 1 in a fourth embodiment according to the present invention shown in FIG. 22, a line L1 is extended from the intersection point P so as to be tangent to a stress relaxing structure 20 and intersects the oblique side edge 6a of an ear part 6 at an intersection point A, and a line L2 is extended from the intersection point Q so as to be tangent to the stress relaxing structure 20 and intersects an extension of the oblique side edge 6a at an intersection point B. Since the intersection point B is a virtual point apart from the ear part 6, an actual second oblique side edge section b' is a portion of a second oblique side edge section b, on the oblique side edge 6a. A fastener 7 is attached to the oblique side edge 6a in a pulling section R partially overlapping the first oblique side edge section a and the actual second oblique side edge section b'. Thus the oblique side edge sections a and b can be defined even if the lines L1 and L2 do not intersect the oblique side edge 6a. In this specification, an expression, "a point where the line L1 (L2) intersects the oblique side edge 6a" has an implication that "a point where the line L1 (L2) intersects an extension of the oblique side edge 6a".

Figure 23:
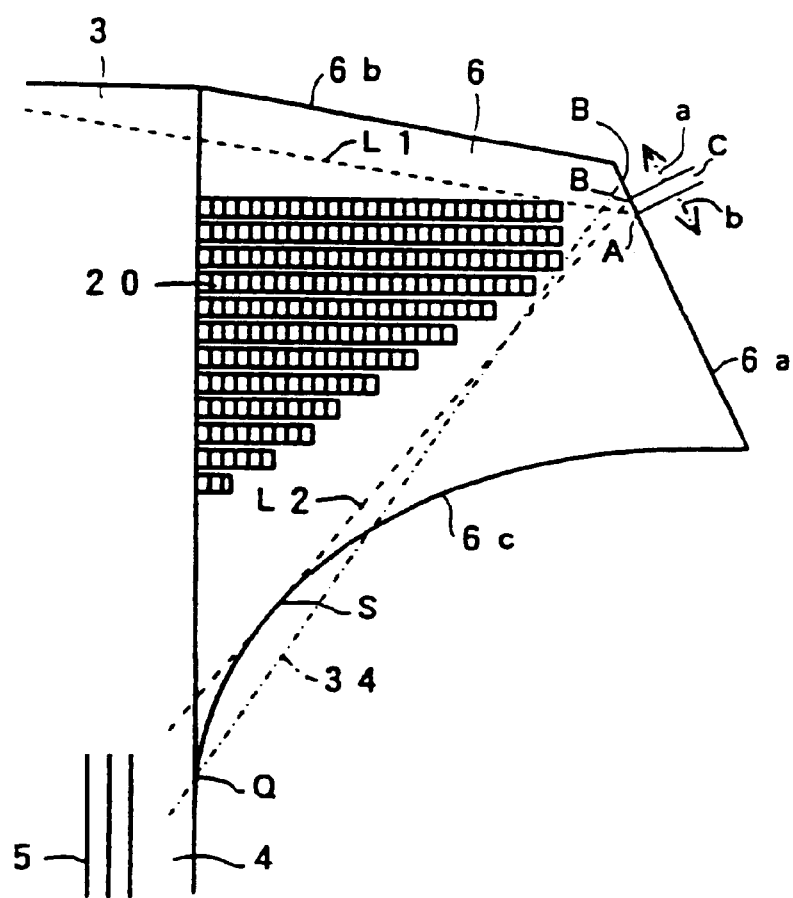
FIG. 23 is a fragmentary development of assistance in explaining a first oblique side edge section a and a second oblique side edge section b of an oblique side edge of an ear part of a disposable diaper in accordance with the present invention.

A disposable diaper 1 in a fifth embodiment according to the present invention is provided with ear parts 6 each having a lower side edge 6c having a lower curved portion S curved in the shape of a circular arc as shown in FIG. 23. A line L2 is tangent to the lower curved portion S of the lower side edge 6c and a stress relaxing structure 20 and intersects the oblique side edge 6a of the ear part 6 at an intersection point B. Therefore, a component tensile force of a tensile force applied to the ear part 6 at the intersection point B can be transmitted, acting along the line L2 can be transmitted to an absorbent part 3. A line 34 extended from the the intersection point of the lower side edge 6c of the ear part 6 and a side flap 4 extended along the side edge of an absorbent part 3 so as to be tangent to the stress relaxing structure 20 intersects the oblique side edge 64 at an intersection point B'. The transmission of a component tensile force of a tensile force applied to the ear part 6 at the intersection point B' and transmitted along the line 34 is intercepted at the intersection point of the line 34 and the lower side edge 6c. In this embodiment, a first oblique side edge section a extends upward from the intersection point A, and a second oblique side edge section b extends downward from the intersection point B. A pulling section R in which a fastener 7 is attached to the oblique side edge 6a must overlap at least a section c between the intersection points A and B in which the first oblique side edge section a and the second oblique side edge section b overlap each other.

The line L2 may be extended from the upper end of one of elastic members 5, i.e., the outermost, the middle or the innermost elastic member 5, instead of from a point on the lower portion of the lower side edge 6c, so as to be tangent to the stress relaxing structure 20. In this case, a component tensile force of a tensile force applied to the ear part 6 at the intersection point B acts directly on the elastic members 5. The line L2 defines a second oblique side edge section b for directly applying a tensile force to the elastic members 5. Although the line L1 for determining the first oblique side edge section a is extended from the intersection point P of the longitudinal center axis L–L' of the absorbent part 3 and the upper edge 1a of the absorbent part 3 in this embodiment, the line L1 may be extended from the right end, as viewed in FIG. 23, of one of elastic members, not shown, i.e., the outermost, the middle or the innermost elastic member, attached to the upper waist lapping portion of the absorbent part 3 so as to be tangent to the stress relaxing structure 20. In this case, a component tensile force of a tensile force applied to the oblique side edge 6a at the intersection point A acts directly on the right ends of the elastic members. Thus, the line L1 defines the first oblique side edge section a for directly applying a component tensile force of a tensile force applied to a fastener 7 to the elastic members.

Figure 24:
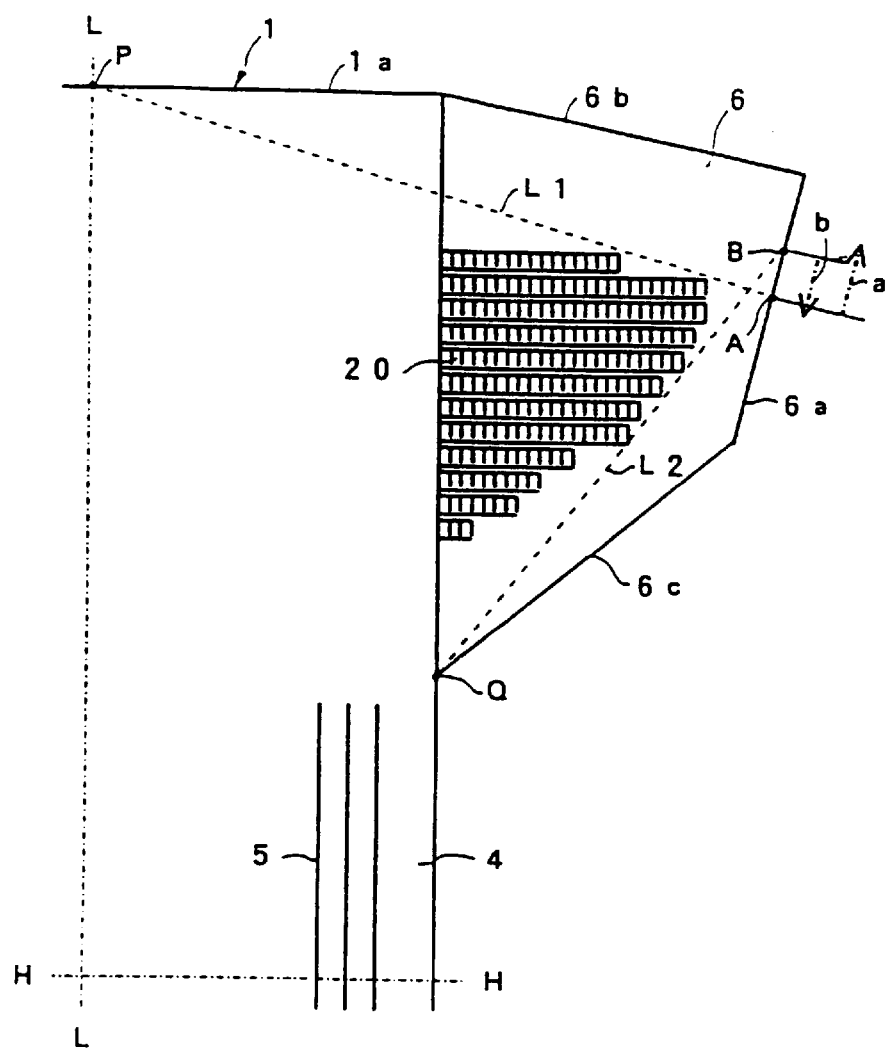
FIG. 24 is a fragmentary development of an ear part in another example.

In a disposable diaper 1 in a sixth embodiment according to the present invention shown in FIG. 24, the oblique side edge 6a' of an ear part 6 extends obliquely downward and toward the longitudinal center axis L–L' of an absorbent part 3 from the outer extremity of the upper side edge 6b of the ear part 6. The inclination, i.e., the angle between the oblique side edge 6a' and a line passing the outer extremity of the upper side edge 6b and parallel to the longitudinal center axis L–L' of the absorbent part 3, meets an inequality: 0<<45. A fastener 7 is attached to the oblique side edge 6a' of the ear part 6 so as to extend perpendicularly to the oblique side edge 6a'.

Supposing the longitudinal center axis L–L' of the absorbent part 3 intersects the upper edge 1a of the absorbent part 3 at an intersection point P, the lower side edge 6c of the ear part 6 intersects a side flap 4 attached to the side edge of the absorbent part 3 at an intersection point Q, a line L1 extends from the intersection point P in tangent to an upper point of a stress relaxing structure 20 on the side of the upper edge 1a and intersects the oblique side edge 6a' at an intersection point A, and a line L2 extends from the intersection point Q in tangent to a lower point of the stress relaxing structure 20 on the side of the transverse center axis H–H' of the absorbent part 3 and intersects the oblique side edge 6a' at an intersection point B, a first oblique side edge section a extends obliquely upward from the intersection point A, and a second oblique side edge section b extends obliquely downward from the intersection point B.

A fastener 7 is attached to the oblique side edge 1a' of the ear part 6 so as to extend perpendicularly to the oblique side edge 6a'. Since the fastener 7 is pulled in a direction perpendicular to the oblique side edge 6a' of the ear part 6, the direction with respect to the longitudinal center axis L–L' of the absorbent part 3 in which the fastener 7 is pulled is dependent on the inclination of the oblique side edge 6a' meeting an inequality: 0<<45. The fastener 7 is pulled perpendicularly to the oblique side edge 6a' regardless of the inclination of the oblique side edge 6a' of the ear part 6. Thus the direction with respect to the longitudinal center line L–L' in which the fastener 7 is pulled is dependent on the inclination of the oblique side edge 6a', the difference between a component tensile force D1 of a tensile force applied to the fastener 7, distributed to a waist lapping portion, and a component tensile force D2 of the same, distributed to a leg lapping portion is small when the inclination of the oblique side edge 6a' is comparatively small, the component tensile force D1 is greater than the component tensile force D2 when the inclination of the oblique side edge 6a' is comparatively large. The fastener 7 is attached to the oblique side edge 6a' of the ear part 6 in a pulling section R. The ratio between the component tensile forces D1 and D2 is dependent on the position of the pulling section R on the oblique side edge 6a'.

As shown in FIG. 1, the fastener 7 of the disposable diaper 1 as packaged is folded back at its middle, and projects from the ear part 6 when the disposable diaper 1 is unfolded for use. The fastener 7 may be formed in the shape of a fork. When thus folded back at the middle, no portion of the fastener 7 projects outward from the ear part 6. When the fastener 7 is formed in the shape of a fork, the tensile force applied to the fastener 7 can be further surely distributed to the waist lapping portion and the leg lapping portion. Since the stress relaxing structure 20 is elastic, the stress relaxing structure 20 conforms easily to the shape of the hipbone and the like, which improves the wearing comfort of the wearer. Although the invention has been described in its preferred forms with a certain degree of particularity, obviously many changes and variations are possible therein. It is therefore to be understood that the present invention may be practiced otherwise than as specifically described herein without departing from the scope and spirit thereof.

What is claimed is:

1. A disposable diaper comprising: an absorbent part formed by sandwiching an absorbent core between a top sheet and a back sheet so that the absorbent core may corresponds to the wearer's crotch when the disposable diaper is put on the wearer, and having a first longitudinal end edge and a second longitudinal end edge; a pair of ear parts projecting in opposite directions from the opposite side edges of one longitudinal end portion of the absorbent part on the side of the first longitudinal end edge, respectively; and one fastening means attached to oblique side edges of the ear parts, respectively;

the oblique side edges of the ear parts to which the fastening means are attached, respectively, being inclined so as to extend at a predetermined angle to the longitudinal center axis of the absorbent part, the fastening means being attached to the oblique side edges of the ear parts so as to extend perpendicularly to the corresponding oblique side edges, respectively, each ear part having a stress relaxing structure, in which a tensile stress smaller than that which is induced in a peripheral portion of the ear part is induced, in a portion thereof other than the peripheral portion, and each fastening means being attached to the ear part in a pulling section of the oblique side edge of the ear part, overlapping at least part of a first side edge section on the oblique side edge of the ear part, extending on the side of the first longitudinal end edge of the absorbent part from an intersection point of the oblique side edge and a first boundary line extending from a point on the first longitudinal end edge so as to be tangent to a point on the stress relaxing structure on the side of the first longitudinal end edge, and part of a second side edge section extending on the side of the lateral center axis of the absorbent part perpendicular to the longitudinal center axis of the absorbent part from the intersection point of the oblique side edge and a second boundary line extending from a point on the side edge of the absorbent part at which the lower end of the ear part joins to the absorbent part so as to be tangent to a point on the stress relaxing structure on the side of the transverse center line.

2. A disposable diaper according to claim 1, wherein the point on the first longitudinal end edge from which the first boundary line extends corresponds to the intersection point of the longitudinal center axis and the first longitudinal end edge.

3. A disposable diaper according to claim 1, wherein the point on the first longitudinal end edge from which the first boundary line extends is the intersection point of the first longitudinal end edge of the absorbent part and the side edge of the absorbent part on the side of the ear part.

4. A disposable diaper according to claim 1, wherein the peripheral portion of the ear part is unstretchable and the stress relaxing structure is stretchable.

5. A disposable diaper according to claim 4, wherein each of the ear parts is formed of an unstretchable material, the stress relaxing structure is formed by processing an unstretchable material so as to be stretchable when tensioned, and the stress relaxing structure does not cause the peripheral portion of the ear part to shrink.

6. A disposable diaper according to claim 5, wherein each of the ear parts is a laminated structure comprising a liquid-impermeable film, a porous film and a nonwoven fabric.

7. A disposable diaper according to claim 1, wherein the peripheral portion of each of the ear parts yields to a high tensile stress and stretches, and the stress relaxing structure yields to a low tensile stress and stretches.

8. A disposable diaper according to claim 1, wherein the oblique side edge of each of the ear parts declines away from the longitudinal center axis of the absorbent part at an inclination to a straight line parallel to the longitudinal center axis of the absorbent part, and the inclination meets an inequality: 0<<45.

9. A disposable diaper according to claim 8, wherein a portion of the pulling section, in which the fastening means is attached to the oblique side edge of the ear part, overlapping the first oblique side edge section is greater than a portion of the same overlapping the second oblique side edge section.

10. A disposable diaper according to claim 9, wherein the pulling section in in which the fastening means is attached to the oblique side edge of the ear part is included in the first oblique side edge section and partly overlaps the second oblique side edge section.

11. A disposable diaper according to claim 1, wherein the oblique side edge of each of the ear parts declines toward the longitudinal center axis of the absorbent part at an inclination to a straight line parallel to the longitudinal center axis of the absorbent part, and the inclination meets an inequality: 0<<45.

12. A disposable diaper according to claim 11, wherein a portion of the pulling section, in which the fastening means is attached to the oblique side edge of the ear part, overlapping the second oblique side edge section is greater than a portion of the same overlapping the first oblique side edge section.

13. A disposable diaper according to claim 12, wherein the pulling section in which the fastening means is attached to the oblique side edge of the ear part is included in the second oblique side edge section and partly overlaps the first oblique side edge section.

14. A disposable diaper comprising: an absorbent part formed by sandwiching an absorbent core between a top sheet and a back sheet so that the absorbent core may correspond to the wearer's crotch when the disposable diaper is put on the wearer, and having a first longitudinal end edge, a second longitudinal end edge, a first waist lapping section contiguous with the first longitudinal end edge, a second waist lapping section contiguous with the second longitudinal end edge, and a crotch lapping section extending between the first and the second waist lapping section; a pair of ear parts projecting from the opposite side edges of the first waist lapping section of the absorbent part; and one fastening means attached to oblique side edges of the ear parts, respectively;

the oblique side edges of the ear parts to which the fastening means are attached, respectively, being inclined at a predetermined inclination to the longitudinal center axis of the absorbent part, the fastening means being attached to the oblique side edges of the ear parts so as to extend perpendicularly to the corresponding oblique side edges, respectively, each ear part having a stress relaxing structure, in which a tensile stress smaller than that which is induced in a peripheral portion of the ear part is induced, in a portion other than the peripheral portion thereof, a portion of the first waist lapping section, extending on the side of the first longitudinal end edge from a first boundary line extending from a point on the first longitudinal end edge so as to be tangent to a point on the stress relaxing structure on the side of the first longitudinal end edge being a waist lapping component force distributing region to which a component tensile force of a tensile force applied to the fastening means acts directly, a section of the oblique side edge of the ear part corresponding to the waist lapping component force distributing region being a first oblique side edge section, a portion of the first waist portion, extending on the side of the crotch lapping section from a second boundary line extending from a point on the side edge of the absorbent part at which the lower end of the ear part joins to the absorbent part so as to be tangent to a point on the stress relaxing structure on the side of the crotch lapping section being a leg lapping component force distributing region to which a component tensile force of a tensile force applied to the fastening means acts directly, a section of the oblique side edge of the ear part corresponding to the leg lapping component force distributing region being a second oblique side edge section, and each fastening means being attached to the ear part in a pulling section of the oblique side edge of the ear part, overlapping at least part of the first side edge section and part of the second side edge section.

15. A disposable diaper according to claim 14, wherein the point on the first longitudinal end edge from which the first boundary line extend corresponds to the intersection point of the longitudinal center axis of the absorbent part and the longitudinal end edge.

16. A disposable diaper according to claim 14, wherein the point on the first longitudinal end edge from which the first boundary line extends is the intersection point of the first longitudinal end edge of the absorbent part and the side edge of the absorbent part on the side of the ear part.

17. A disposable diaper according to claim 14, wherein the oblique side edge of each of the ear parts declines away from the longitudinal center axis of the absorbent part at an inclination to a straight line parallel to the longitudinal center axis of the absorbent part, and the inclination meets an inequality: 0<<45.

18. A disposable diaper according to claim 17, wherein a portion of the pulling section, in which the fastening means is attached to the oblique side edge of the ear part, overlapping the first oblique side edge section is greater than a portion of the same overlapping the second oblique side edge section.

19. A disposable diaper according to claim 18, wherein the pulling section, in which the fastening means is attached to the oblique side edge of the ear part, is included in the first oblique side edge section and partly overlaps the second oblique side edge section.

20. A disposable diaper according to claim 14, wherein the oblique side edge of each of the ear parts declines toward the longitudinal center axis of the absorbent part at an inclination to a straight line parallel to the longitudinal center axis of the absorbent part, and the inclination meets an inequality: 0<<45.

21. A disposable diaper according to claim 20, wherein a portion of the pulling section, in which the fastening means is attached to the oblique side edge of the ear part, overlapping the second oblique side edge section is greater than a portion of the same overlapping the first oblique side edge section.

22. A disposable diaper according to claim 12, wherein the pulling section in which the fastening means is attached to the oblique side edge of the ear part is included in the second oblique side edge section and partly overlaps the first oblique side edge section.

23. A disposable diaper comprising; an absorbent part formed by sandwiching an absorbent core between a top sheet and a back sheet so that the absorbent core may correspond to the wearer's crotch when the disposable diaper is put on the wearer, and having a first longitudinal end edge, a second longitudinal end edge, a first waist lapping section contiguous with the first longitudinal end edge, a second waist lapping section contiguous with the second longitudinal end edge, and a crotch lapping section extending between the first and the second waist lapping section; elastic leg fastening means extended along the opposite side edges of the crotch lapping section of the absorbent part, respectively; a pair of ear parts projecting from the opposite side edges of the first waist lapping section of the absorbent part; and one fastening means attached to oblique side edges of the ear parts, respectively;

the oblique side edges of the ear parts to which the fastening means are attached, respectively, being inclined at a predetermined inclination to the longitudinal center axis of the absorbent part, the fastening means being attached to the oblique side edges of the ear parts so as to extend perpendicularly to the corresponding oblique side edges, respectively, each ear part having a stress relaxing structure, in which a tensile stress smaller than that which is induced in a peripheral portion of the ear part is induced, in a portion other than the peripheral portion thereof, a portion of the first waist lapping section, extending on the side of the first longitudinal end edge from a first boundary line extending from a point on the first longitudinal end edge so as to be tangent to a point on the stress relaxing structure on the side of the first longitudinal end edge being a waist lapping component force distributing region to which a component tensile force of a tensile force applied to the fastening means acts directly, a section of the oblique side edge of the ear part corresponding to the waist lapping component force distributing region being a first oblique side edge section, a portion of the first waist portion, extending on the side of the crotch lapping section from a second boundary line extending from one end of the leg fastening means on the side of the first longitudinal side edge so as to be tangent to a point on the stress relaxing structure on the side of the crotch lapping section being a leg lapping component force distributing region to which a component tensile force of a tensile force applied to the fastening means acts directly, a section of the oblique side edge of the ear part corresponding to the leg lapping component force distributing region being a second oblique side edge section, and each fastening means being attached to the ear part in a pulling section of the oblique side edge of the ear part, overlapping at least part of the first side edge section and part of the second side edge section.

24. A disposable diaper comprising; an absorbent part formed by sandwiching an absorbent core between a top sheet and a back sheet so that the absorbent core may correspond to the wearer's crotch when the disposable diaper is put on the wearer, and having a first longitudinal end edge, a second longitudinal end edge, a first waist lapping section contiguous with the first longitudinal end edge, a second waist lapping section contiguous with the second longitudinal end edge, and a crotch lapping section extending between the first and the second waist lapping section; elastic waist fastening means extended along the first longitudinal end edge in the first waist lapping section; a pair of ear parts projecting from the opposite side edges of the first waist lapping section of the absorbent part; and one fastening means attached to oblique side edges of the ear parts, respectively;

the oblique side edges of the ear parts to which the fastening means are attached, respectively, being inclined at a predetermined inclination to the longitudinal center axis of the absorbent part, the fastening means being attached to the oblique side edges of the ear parts so as to extend perpendicularly to the corresponding oblique side edges, respectively, each ear part having a stress relaxing structure, in which a tensile stress smaller than that which is induced in a peripheral portion of the ear part is induced, in a portion other than the peripheral portion thereof, a portion of the first waist lapping section, extending on the side of the first longitudinal end edge from a first boundary line extending from one end of the elastic waist fastening means on the side of the ear part so as to be tangent to a point on the stress relaxing structure on the side of the first longitudinal end edge being a waist lapping component force distributing region for directly applying a component tensile force of a tensile force applied to the fastening means to the one end of the elastic waist fastening means, a section of the oblique side edge of the ear part corresponding to the waist lapping component force distributing region being a first oblique side edge section, a portion of the first waist lapping portion, extending on the side of the crotch lapping section from a second boundary line extending from a point on a side edge of the ear part on the side of the crotch lapping section so as to be tangent to a point on the stress relaxing structure on the side of the crotch lapping section being a leg lapping component force distributing region for directly applying a component tensile force of a tensile force applied to the fastening means to the point on the side edge of the ear part on the side of the crotch lapping section, a section of the oblique side edge of the ear part corresponding to the leg lapping component force distributing region being a second oblique side edge section, and each fastening means being attached to the ear part in a pulling section of the oblique side edge of the ear part, overlapping at least part of the first side edge section and part of the second side edge section.

25. A disposable diaper comprising; an absorbent part formed by sandwiching an absorbent core between a top sheet and a back sheet so that the absorbent core may correspond to the wearer's crotch when the disposable diaper is put on the wearer, and having a first longitudinal end edge, a second longitudinal end edge, a first waist lapping section contiguous with the first longitudinal end edge, a second waist lapping section contiguous with the second longitudinal end edge, a crotch lapping section extending between the first and the second waist lapping section; elastic leg fastening means extended along the opposite longitudinal side edges of the crotch lapping section; elastic waist fastening means extended along the first longitudinal end edge of the absorbent part in the first waist lapping section; a pair of ear parts attached to the first waist lapping section of the absorbent part; and one fastening means attached to oblique side edges of the ear parts, respectively;

the oblique side edges of the ear parts to which the fastening means are attached, respectively, being inclined at a predetermined inclination to the longitudinal center axis of the absorbent part, the fastening means being attached to the ear parts so as to extend perpendicularly to the corresponding oblique side edges, respectively, each ear part having a stress relaxing structure, in which a tensile stress smaller than that which is induced in a peripheral portion of the ear part is induced, in a portion thereof other than the peripheral portion, a portion of the first waist lapping section, extending on the side of the first longitudinal end edge from a first boundary line extending from one end of the elastic waist fastening means on the side of the ear part so as to be tangent to a point on the stress relaxing structure on the side of the first longitudinal end edge being a waist lapping component force distributing region for directly applying a component tensile force of a tensile force applied to the fastening means to the one end of the elastic waist fastening means, a section of the oblique side edge of the ear part corresponding to the waist lapping component force distributing region being a first oblique side edge section, a portion of the first waist portion, extending on the side of the crotch lapping section from a second boundary line extending from one end of the elastic leg fastening means on the side of the first longitudinal side edge so as to be tangent to a point on the stress relaxing structure on the side of the crotch lapping section being a leg lapping component force distributing region for directly applying a component tensile force of a tensile force applied to the fastening means to the one end of the elastic leg fastening means, a section of the oblique side edge of the ear part corresponding to the leg lapping component force distributing region being a second oblique side edge section, and each fastening means being attached to the ear part in a pulling section of the oblique side edge of the ear part, overlapping at least part of the first side edge section and part of the second side edge section.

* * * * *

UNITED STATES PATENT AND TRADEMARK OFFICE
CERTIFICATE OF CORRECTION

PATENT NO. : 5,906,008
DATED : May 25, 1999
INVENTOR(S) : Heki et al.

It is certified that error appears in the above-identified patent and that said Letters Patent is hereby corrected as shown below:

Title page,
Item [22], PCT filling date, after "PCT Filed:" please delete "Apr. 3, 1996" and insert therefor -- Mar. 4, 1996 --.

Column 5,
Line 32, after "edge" please insert -- , -- (a comma).

Column 18,
Line 35, please delete "an" and insert therefor -- the --.

Column 19,
Line 22, please delete the second occurrence of "in".
Line 65, please delete "a" and insert therefor -- the --.

Column 21,
Line 28, please delete "a" and insert therefor -- the --.

Column 22,
Line 15, please delete "a" and insert therefor -- the --.

Column 23,
Line 7, please delete "a" and insert therefor -- the --.

Signed and Sealed this

Twentieth Day of July, 2004

JON W. DUDAS
*Acting Director of the United States Patent and Trademark Office*